(12) United States Patent
Aksan et al.

(10) Patent No.: US 9,492,271 B2
(45) Date of Patent: Nov. 15, 2016

(54) SILICA-BASED COMPOSITE OCULAR DEVICE AND METHODS

(75) Inventors: Alptekin Aksan, Minneapolis, MN (US); Allison Hubel, St. Paul, MN (US); Eduardo Reategui, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 584 days.

(21) Appl. No.: 13/577,572

(22) PCT Filed: Feb. 8, 2011

(86) PCT No.: PCT/US2011/024032
§ 371 (c)(1),
(2), (4) Date: Oct. 29, 2012

(87) PCT Pub. No.: WO2011/097619
PCT Pub. Date: Aug. 11, 2011

(65) Prior Publication Data
US 2013/0204363 A1 Aug. 8, 2013

Related U.S. Application Data

(60) Provisional application No. 61/302,362, filed on Feb. 8, 2010.

(51) Int. Cl.
| | | |
|---|---|---|
| *A61K 38/00* | (2006.01) | |
| *A61F 2/14* | (2006.01) | |
| *A61L 27/24* | (2006.01) | |
| *G02B 1/04* | (2006.01) | |

(52) U.S. Cl.
CPC ............... *A61F 2/142* (2013.01); *A61L 27/24* (2013.01); *G02B 1/043* (2013.01); *A61L 2400/12* (2013.01); *A61L 2430/16* (2013.01)

(58) Field of Classification Search
None
See application file for complete search history.

(56) References Cited

U.S. PATENT DOCUMENTS

| | | | |
|---|---|---|---|
| 3,955,012 A | 5/1976 | Okamura et al. | |
| 4,470,159 A | 9/1984 | Peyman | |
| 4,676,790 A | 6/1987 | Kern | |
| 5,286,829 A * | 2/1994 | Fedorov et al. | 527/201 |
| 5,354,332 A | 10/1994 | Lacombe | |
| 5,433,745 A | 7/1995 | Graham et al. | |
| 5,836,313 A | 11/1998 | Perez et al. | |
| 5,843,185 A | 12/1998 | Rolden et al. | |
| 6,005,160 A | 12/1999 | Hsiue et al. | |
| 6,106,552 A | 8/2000 | Lacombe et al. | |
| 6,508,837 B1 | 1/2003 | Silvestrini | |
| 6,755,858 B1 | 6/2004 | White | |
| 6,814,755 B2 | 11/2004 | Lacombe et al. | |
| 6,897,271 B1 | 5/2005 | Domschke et al. | |
| 6,976,997 B2 | 12/2005 | Noolandi et al. | |
| 7,364,674 B1 | 4/2008 | Hoover | |
| 2006/0083773 A1* | 4/2006 | Myung et al. | 424/427 |

FOREIGN PATENT DOCUMENTS

| | | | | |
|---|---|---|---|---|
| WO | WO2008/109886 | * | 9/2008 | ............... A61F 2/02 |
| WO | 2011/038485 A1 | | 4/2011 | |
| WO | 2011/097619 A2 | | 8/2011 | |

OTHER PUBLICATIONS

Abelson et al., "Normal Human Tear pH by Direct Measurement," *Archives of Opthalmology*, Feb. 1981; 99:301.
Aiken-O'Neill et al., "Summary of Corneal Transplant Activity," *Cornea*, 2002; 21:1-3.
Aksan et al., "Roles of Thermodynamic State and Molecular Mobility in Biopreservation," in *Biomedical Engineering Handbook: Tissue Engineering and Artificial Organs*, CRC Press, Boca Raton, FL, 2006; 41.1-41.20.
Aksan et al., "Desiccation Kinetics of Biopreservation Solutions in Microchannels," *Journal of Applied Physics*, 2006; 99:2181280.
Aksan et al., "Thermal Damage Prediction for Collagenous Tissues Part I: A Clinically Relevant Numerical Simulation Incorporating heating Rate Dependant Denaturation," *J of Biomechanical Eng.*, Feb. 2005; 127:85-97.
Aksan et al., "Analysis of Desiccation and Vitrification Characteristics of Carbohydrate Films by Shear-Wave Resonators," *Langmuir*, 2005; 21:2847-2854.
Aksan et al., "Isothermal Desiccation and Vitrification Kinetics of Trehalose-Dextran Solutions," *Langmuir*, 2004; 20:5521-5529.
Aksan et al., "Thermomechanical Analysis of Soft Tissue Thermotherapy," *J. of Biomechanical Eng.*, Oct. 2003; 125:700-708.
Aksan et al., "Effects of Thermal Damage on the Mechanical Properties of Collagenous Tissues," *Technology and Health Care.*, 2002; 10:281-283.
Alvarez-Lorenzo et al., "Contact Lenses for Drug Delivery," *Am. J. Drug Del.*, 2006, 4(3):131-151.
Andreassen et al., "Biomechanical properties of keratoconus and normal corneas," *Exp Eye Res.*, Oct. 1980; 31(4):435-441.
Armitage et al., "Predicting Endothelial Cell Loss and Long-Term Corneal Graft Survival," *Invest Opthalmol Vis Sci.*, 2003; 44:3326-3331.
Arnoczky et al., "Thermal Modification of connective Tissues: Basic Science Considerations and Clinical Implications," *Journal of the Am. Acad of Orthopaedic Surgeons*, 2000; 8:305-313.
Avnir et al., "Recent Bio Applications of Sol-Gel Materials," *J. Materials Chemistry*, 2006;16:1013-1030.
Bahn et al., "Penetrating Keratoplasty in the Cat. A Clinically Applicable Model," *Ophthalmology*, 1982; 89:687-99.
Balasubramanian et al., "Water Transport and IIF parameters for a Connective Tissue Equivalent," *Cryobiology*, 2006; 52:62-73.
Baratz et al., "Effects of Glaucoma Medications on Corneal Endothelium Keratocytes, and Subbasal Nerves Among Participants in the Ocular Hypertension Treatment Study," *Cornea*, 2006; 25:1046-1052.

(Continued)

*Primary Examiner* — Jeanette Lieb
(74) *Attorney, Agent, or Firm* — Mueting, Raasch & Gebhardt, P.A.

(57) ABSTRACT

Disclosed herein are synthetic silica-based ocular devices fabricated from a composite material comprising silica and a fibrillar protein, together with methods of making and using the ocular devices.

15 Claims, 16 Drawing Sheets

(56) References Cited

OTHER PUBLICATIONS

Beck et al., "Is donor age an important determinant of graft survival?" *Cornea*, Sep. 1999; 18(5):503-510.

Bell et al., "Pathology of Late Endothelial Failure: Late Endothelial Failure of Penetrating Keratoplasty: Study with Light and Electron Microscopy," *Cornea*, 2000; 19(1):40-46.

Bidault et al., "Water Content in an Engineered Dermal Replacement During Permeation of $Me_2SO$ Solutions Using MR Imaging," *Biotechnol Prog*, 2001; 17:530-536.

Bidault et al., "Rapid MR Imaging of Cryoprotectant Permeation in an Engineered Dermal Replacement," *Cryobiology*, 2000; 40:13-26.

Billiar et al., "Effects of carbodiimide crosslinking conditions on the physical properties of laminate intestinal submucosa," *Journal of Biomedical Materials Research*, Jul. 2001; 56(1):101-108. Available online Apr. 1, 2001.

Borene et al., "Mechanical Characterization and Phenotype Assessment of Corneal Fibroblasts Cultured in a Three-Dimensional Collagen Matrix," *Ann. Biomedical Engineering*, Feb. 2004; 32(2):274-283.

Bourne et al., "Clinical Responses of the Corneal Endothelium," *Exp Eye Res*, 2004; 78:561-572.

Bourne et al., "Biology of the Corneal Endothelium in Health and Disease," *Eye*, 2003; 17:912-918.

Bourne, "Cellular Changes in Transplanted Human Corneas," *Cornea*, 2001; 20(6):560-569.

Bourne et al., "Comparison of Chen Medium and Optisol-GS for Human Corneal Preservation at 4° C: Results of transplantation," *Cornea*, 2001; 20(7):683-686.

Bourne, "The Effect of Long-Term Contact Lens Wear on the Cells of the Cornea," *CLAO J.*, Oct. 2001; 27:225-230.

Bourne et al., "Comparison of Three methods for Human Corneal Cyropreservation that Utilize Dimethyl Sulfoxide," *Cyrobiology*, 1999; 39:47-57.

Bourne et al., "Estimation of Corneal Endothelial Pump Function in Long-Term Contact Lens Wearers," *Invest. Ophthalmol. Vis. Sci.*, 1999; 40:603-611.

Brasack et al., "Biocompatibility of modified silica-protein composite layers," *Journal of Sol-Gel Science and Technology*, Dec. 2000; 19:479-482.

Brown et al., "Automated Stromal Nerve Rejection in Corneal Confocal Images in vivo," Paper presented at SPIE Conference: *Medical Imaging 2000: Image Processing, Proceedings of SPIE*, published Jun. 6, 2000.

Brubaker et al., "Ascorbic Acid Content of human Corneal Epithelium," *Invest. Ophthalmol. Vis. Sci.*, 2000; 41:1681-1683.

Brunette et al., "A system for long-term corneal perfusion," *Investigative Ophthalmology & Visual Science*, Aug. 1989; 30(8):1813-1822.

Bryans et al., "Microstructure and Porosity of Silica Xerogel Monoliths Prepared by the Fast Sol-Gel Method," *J. Sol-Gel SciTech*, 2000; 17:211-217.

Bryant et al., "Corneal Tensile Strength in Fully Healed Radial Keratotomy Wounds," *Invest. Ophthalmol. Vis. Sci.*, 1994; 35:3022-31.

Burger et al., "Development of Infusible-Grade Solution for Non-Cryopreserved Hematopoietic Cell Storage," *Crytotherapy*, 1999; 1(2):123-133.

Buzard, "Introduction to Biomechanics of the Cornea," *Refract. Corneal Surg.*, Mar./Apr. 1992; 8:127-38.

Calvillo et al., "Corneal Reinnervation after LASIK: Prospective 3-Year Longitudinal Study," *Invest. Ophthalmol. Vis. Sci.*, 2004; 45:3991-3996.

Carlson et al., "Variations in Human Corneal Endothelial Cell Morphology and Permeability to Fluorescein with Age," *Exp Eye Res.*, 1988; 47:27-41.

Carlson et al., "Effect of Body Position on Intraocular Pressure and Aqueous Flow," *Invest. Ophthalmol. Vis. Sci.*, 1987; 28:1346-1352.

Carlsson et al., "Bioengineered Corneas: How Close Are We?" *Current Opinion in Ophthalmology*, 2003; 14:192-197.

Chang et al., "Modeling the Interaction of Biological Cells with a Solidifying Interface," *J Computational Phys.*, 2007; 226:1808-1829.

Christiansen et al., "Mechanism of Ocular Hypotensive action of Bimatoprost (Lumigan) in Patients with Ocular Hypertension or Glaucoma," *Ophthalmology*, 2004; 111:1658-1662.

Chu, "The Past Twenty-Five Years in Eye Banking," *Cornea*, 2000; 19(5):754-765.

Coradin et al., "Sol-gel biopolymer/silica nanocomposites in biotechnology," *Current Nanosicence*, Aug. 2006; 2(3):219-230.

Coradin et al., "A novel route to collagen-silica biohybrids," *Material Research Society Symposium Proceedings*, 2002; 726:79-83.

Crabb et al., "Influence of Matrix Processing on the Optical and Biomechanical Properties of a Corneal Stromal Equivalent," *Tissue Eng. Part A*, Nov. 1, 2008; 14:173-182.

Crabb et al., "Microstructural Characteristics of Extracellular Matrix Produced by Stromal Fibroblasts," *Ann Biomed. Engr.*, Oct. 2006; 34(10):1615-1627.

Crabb et al., "Biomechanical and Microstructural Characteristics of a Collagen Film-Based Corneal Stromal Equivalent," *Tissue Eng.*, 2006; 12:1565-1575.

Darr et al., "Freezing Characteristics of Isolated Pig and Human Hepotocytes," *Cell Transplant*, 1997; 6(2):173-183.

Darr et al., "Investigation of Sub Zero Water Transport Properties for Isolated Hepotocytes and Hepotocytes Cultured in Spheroids," *Trans Am Soc Mech Eng., Bioeng Div.*, 1995; 29:269-270.

Dehring et al., "Correlating Changes in Collagen Secondary Structure with Aging and Defective Type II Collagen by Raman Spectroscopy," *Appl. Spectroscopy* 2006; 60:366-372.

Delamere et al., "Production of $PGE_2$ by Bovine Cultured Airway Smooth Muscle Cells and its Inhibition by Cyclo-Oxygenase Inhibitors," *Br J. Pharmacol*, 1994; 111:983-988.

Desimone et al., "Fibroblast encapsulation in hybrid silica-collagen hydrogels," *Journal of Materials Chemistry*, 2010; 20(4):666-668. Available online Dec. 10, 2009.

Dinslage et al., "Intraocular Pressure in Rabbits by Telemetry II: Effects of Animal Handling and Drugs," *Invest Ophthalmol Vis Sci.*, 1998; 39:2485-2489.

Doillon et al., "A Collagen-Based Scaffold for a Tissue Engineered Human Cornea: Physical and Physiological Properties," *Int J. Artif Organs*, 2003; 26(8):764-773.

Duan et al., "Dendrimer Crosslinked Collagen as a Corneal Tissue Engineering Scaffold: Mechanical Properties and Corneal Epithelial Cell Interactions," *Biomaterials*, 2006; 27:4608-17. Available online May 19, 2006.

Duncan et al., "Flow-manipulated, crosslinked collagen gels for use as corneal equivalents," *Biomaterials*, Dec. 2010; 31(34):8996-9005.

Egan et al., "Analysis of Telomere Lengths in Human Corneal Endothelial Cells From Donors of Different Ages," *Invest Ophthalmol Vis Sci.*, 1998; 39:648-653.

Egan et al., "Effect of Dorzolamide on Corneal Endothelial Function in Normal Human Eyes," *Invest Ophthalmol Vis Sci.*, 1998; 39:23-29.

Eglin et al., "Comparative Study of the Influence of Several Silica Precursors on Collagen Self-Assembly and of Collagen on 'Si' Speciation and Condensation," *J. Mat. Chem.* 2006; 16:2220-2230. Available online Sep. 12, 2006.

Eglin et al., "Collagen-Silica Hybrid Materials: Sodium Silicate and Sodium Chloride Effects of Type I Collagen Fibrillogenesis," *Biomed. Mater Eng.*, 2005; 15:43-50.

Elsheikh et al., "Biomechanical properties of human and porcine corneas," *Exp. Eye Res.*, May 2008; 86(5):783-790.

Elsheikh et al., "Assessment of Corneal Biomechanical Properties and Their Variation with Age," *Cur Eye Res.*, Jan. 2007; 32(1):11-19.

Erie et al., "Confocal microscopy in ophthalmology," *American Journal of Ophthalmology*, Nov. 2009; 148(5):639-646.

Erie, "Corneal Nerve Morphology and Function After Bladeless and MIcrokeratome LASIK. A Randomized-Controlled Study," *Invest. Ophthalmol Vis Sci.*, 2006; 47:E-Abstract 516.

(56) References Cited

OTHER PUBLICATIONS

Erie et al., "Corneal Keratocyte Deficits after Photorefractive Keratectomy and Laser in Situ Keratomileusis," *Am. J. Ophthalmol.*, May 2006; 141:799-809.
Erie et al., "Long-Term Corneal Keratocyte Deficits after Photorefractive Keratectomy and Laser in Situ Keratomileusis," *Trans. Am. Ophthalmol Soc.*, 2005; 103:56-68.
Erie et al., "Recovery of Corneal Subbasal Nerve Density after PRK and LASIK," *Trans. Am. Ophthalmol.*, 2005; 140:1059-1064.
Erie et al., "The Effect of Age on the Corneal Subbasal Nerve Plexus," *Cornea*, Aug. 2005; 24(6):705-09.
Erie et al., "Confocal Microscopy Evaluation of Stromal Ablation Depth after Myopic Laser in Situ Keratomileusis and Photorefractive Keratectomy," *J. Cataract Refract Surg*, 2004; 30:321-325.
Erie et al., "Long-Term Keratocyte Deficits in the Corneal Stroma after LASIK," *Ophthalmology*, 2004; 111:1356-1361.
Erie et al., "Keratocyte Density in the Human Cornea After Photorefractive Keratectomy," *Arch. Ophthalmol*, 2003; 121:770-776.
Erie et al., "Aberrant Corneal Nerve Regeneration after PRK," *Cornea*, Oct. 2003; 22(7):684-686.
Erie et al., "Effect of Myopic Laser in Situ Keratomileusis on Epithelial and Stromal Thickness: A Confocal Microscopy Study," *Ophthalmol gy*, 2002; 109:1447-1452.
Erie et al., "Keratocyte Density in Keratoconus. A Confocal Microscopy Study," *Am. J. Ophthalmol*, 2002;134:689-95.
Erie et al., "Keratocyte Density in Vivo After Photorefractive Keratectomy in Humans," *Trans. Am. Ophthalmol Soc.*, 1999; 97:221-240.
Ethier et al., "Ocular Biomechanics and Biotransport," *Ann Rev. Biomed. Eng.*, 2004; 6:249-73.
Evans et al., "Progress in the Development of a Synthetic Corneal Onlay," *Investigative Ophthalmology & Visual Science*, 2002; 43:3196-201.
Evans et al., "The use of Corneal Organ Culture in Biocompatibility Studies," *Biomaterials*, 2002; 23:1359-67.
Evans et al., "Epithelialization of a synthetic polymer in the feline cornea: a preliminary study," *Investigative Ophthalmology & Visual Science*, 2000; 41:1674-80.
Eye Bank Association of America, "2010-2011 A Year in Review," Washington, DC, 2011; 18 pgs.
Eye Bank Association of America, "2010 Annual Statistical Report," Washington, DC, 2010; 18pgs.
Eye Bank Association of America, "2004 Eye Banking Statistical Report," Washington DC, 2005; 15 pages.
Faia et al., "Corneal Graft Folds: A Complication of Deep Lamellar Endothelial Keratoplasty," *Arch. Ophthalmol.*, 2006;124:593-595.
Fagerholm et al., "A biosynthetic alternative to human donor tissue for inducing corneal regeneration: 24-month follow-up of a phase 1 clinical study," *Science Translational Medicine*, Aug. 25, 2010; 2(46):ra61.
Fagerholm et al., "Corneal regeneration following implantation of a biomimetic tissue-engineered substitute," *Clinical and Translational Science*, Apr. 2009; 2(2):162-164.
Farrell et al., "Interaction of Light and the Cornea: Absorption versus Wavelength," Abstract from *The Cornea:* Transactions of the World Congress on the Cornea III., Raven Press, New York, NY, 1998; 173-179.
Farrell et al., "Wave-length Dependencies of Light Scattering in Normal and Cold Swollen Rabbit Corneas and their Structural Implications," *J. Physiology*, 1973; 233:589-612.
Figliola et al., *Theory and Design for Mechanical Measurements, 4th Edition*, John Wily& Sons, Inc., Hoboken, NJ; 2006: pp. 120-124, 148-179.
Fleming et al., "Cryopreservation of Hematopoietic Stem Cells: Emerging Science, Technology and Issues," *Trans Med Hemother*, 2007; 34:268-275.
Fleming et al., "Numerical Characterization of Diffusion-Based Extraction in Cell Laden Flow Through a Microfludic Device," *J Bio. Mech Engr.*, Oct. 2007; 129:703-711.
Fleming et al., "Cryopreservation of Hematopoietic and Non-Hematopoietic Stem Cells," *Trans Apheresis Sci.*, 2006; 34:309-315.
Fleming Glass et al., "Optimization of a Microfluidic Device for Diffusion-Based Extraction of DMSO from a Cell Suspension," *Int. J Heat Transfer*, Nov. 2008; 51:5749-5757.
Flickinger et al., "Painting and Printing Living Bacteria: Engineering Nanoporous Biocatalytic Coatings to Preserve Microbial Viability and Intensify Reactivity," *Biotechnology Progress*, 2007; 23:2-17.
Freund et al., "Effects of Fibril Orientations on Light Scattering in the Cornea," *J. Optical Soc. America.*, Nov. 1986; 3(11):1970-1982.
Frushour et al., "Raman Scattering of Collagen, Gelatin and Elastin," *Biopolymers* 1975; 14:379-391.
Fung, *Biomechanics: Mechanical Properties of Living Tissues. 2nd Edition*, Springer, New York, NY, 1993; pp. 274 and 277.
Gailliez-Degremont et al., "Polyamines Adsorbed onto Silica Gel: A Raman Microprobe Analysis," *Journal of Applied Polymer Science*, 1998; 65:871-882.
Griffith et al., "Artificial human corneas: scaffolds for transplantation and host regeneration," *Cornea*, 2002; 21(Suppl. 2):S54-S61.
Griffith et al., "Functional Human Corneal Equivalents Constructed from Cell Lines," *Science*, 1999; 286:2169-2172.
Guo et al., "Morphologic characterization of organized extracellular matrix deposition by ascorbic acid-stimulated human corneal fibroblasts," *Invest Ophthalomol Vis Sci.*, 2007; 48:4050-60.
Haynes et al., "Optical Properties of Selected Organic and Inorganic Materials," *CRC Handbook of Chemistry and Physics*, $92^{nd}$ edition, CRC Press/Taylor and Francis, Boca Raton, FL; 2012; 163-164.
Heier et al., "Ocular injuries and diseases at a combat support hospital in support of Operations Desert Shield and Desert Storm," *Arch Ophthalmol*, Jun. 1993; 111:795-798.
Heinemann et al., "Bioactive Silica-Collagen Composite Xerogels Modified by Calcium Phosphate Phases with Adjustable Mechanical Properties for Bone Replacement," *Acta Biomater*, 2009; 5:1979-1990.
Heinemann et al., "A Novel Biomimetic Hybrid Material Made of Silicified Collagen: Perspectives for Bone Replacement," *Adv. Engr. Mats*, 2007; 9:1061-1068.
Herman et al., "Changes in Corneal Thickness in Patients with treated and Untreated Ocular Hypertension," *Cornea*, 2006; 25:639-643.
Hicks et al., "Corneal Replacement Using a Synthetic Hydrogel Cornea, AlphaCor™: Device, Preliminary Outcomes and Complications," *Constable Eye*, 2003; 17:385-92.
Huang-Lee et al., "Biochemical Changes and Cytotoxicity Associated with the Degradation of Polymeric Glutaraldehyde Derived Crosslinks," *J. Biomed. Mater. Res.*, 1990; 24:1185-1201.
Hubel et al., "Novel Biocomposite Corneal Replacement," Abstract, XIX Biennial Meeting of the International Society for Eye Research, Montreal, Canada, Jul. 23, 2010; 1 pg.
Hubel et al., "Cell Partitioning During the Directional Solidification of Trehalose Solutions," *Cryobiology*, 2007; 55:182-188. Available online Jul. 14, 2007.
Hubel et al., "Frontiers in Clinical Research: Post-Thaw Function and Caspase Activity of Cryopreserved Hepatocyte Aggregates," *Cell Preserve Tech.*, 2004; 2(3):164-171.
Hubel et al., "Liquid Storage, Shipment and Cryopreservation of Cord Blood," *Transfusion*, Apr. 2004; 44:518-525.
Hubel et al., "Cryopreservation of Cord Blood After Liquid Storage," *Cytotherapy*, 2003; 5(5):370-6.
Hubel et al., "Short-Term Liquid Storage of Umbilical Cord Blood," *Transfusion*, May 2003; 43:626-632.
Hubel et al., "Migration of Corneal Epithelium on a Collagen Sponge in Vitro and in Vivo," *Trans Am Soc Mech Eng., Bioengineering Conference*, 2001; 50:351-352.
Hubel et al., "Freezing Characteristics of Genetically Modified Lymphocytes for the Treatment of MPS II," *Cell Transplant.*, 1999; 8:521-530.
Hubel et al., "The Role of Surface Modification on the Culture and Transduction of Hematopoietic Cells for Gene Therapy," *Trans Am Soc Mech Eng, Bioeng Div.*, 1999; 42:7-8.

(56) References Cited

OTHER PUBLICATIONS

Hubel et al., "Cryobiophysical Characteristics of Genetically Modified Hematopoietic Progenitor Cells," *Cryobiolog.*, 1999; 38:140-153.

Hubel et al., "Survival of Directionally Solidfied B-Lymphoblasts Under Various Crystal Growth Conditions," *Cryobiology*, 1992; 29:183-198.

Hubel et al., "Intracellular Ice Formation During the Freezing of Hepatocytes Cultured in a Double Collagen Gel," *Biotechnol Prog.*, 1991; 7:554-559.

Ing et al., "Ten-Year Postoperative Results of Penetrating Keratoplasty," *Ophthalmology* 1998; 105(10):1855-1865.

International Search Report, mailed Sep. 2, 2011, Patent Application No. PCT/US2011/024032, filed Feb. 8, 2011.

International Preliminary Report on Patentability and Written Opinion, issued Aug. 14, 2012, Patent Application No. PCT/US2011/024032, filed Feb. 8, 2011.

Jayasuriya et al., "Piezoelectric and mechanical properties in bovine cornea," *Journal of Biomedical Materials Research A*, 2003; 66:260-265.

Kadler et al., "Collagen Fibril Formation," *Biochem. J.*, 1996; 316:1-11.

Kelley et al., "A Primate Model of Human Corneal Transplantation," *Invest. Ophthalmol. Vis. Sci.*, 1984; 25:1061-4.

Kitzmann et al., "Confocal Microscopy of a Femtosecond laser LASIK Flap before Separation," Am J. Ophthalmol, 2007; 143:691-693.

Kitzmann et al., "Comparison of Corneal Endothelial Cell Images From a Noncontact Specular Microscope and a Scanning Confocal Microscope," *Cornea*, Nov. 2005; 24:980-984.

Komuro et al., "Cell Death During Corneal Storage at 4° C.," *Invest. Ophthalmol. Vis. Sci.*, 1999; 40:2827-2832.

Korniski et al., "A Model of Low-Temperature Water Transport for Hepatocyte Spheroids," *Ann NY Acad Sci*, 1998; 858:183-190.

Lang et al., "A New Morphologic Manifestation of Langerhans Cells in Guinea Pig Corneal Transplants," *Current Eye Research*, 1981; 1:161-7.

Lee et al., "Reiinnervation in the Cornea after LASIK," *Invest. Opthalmol Vis Sci.*, 2002; 43:3660-3664.

Li et al., "Cellular and nerve regeneration within a biosynthetic extracellular matrix for corneal transplantation," *Proc Natl Acad Sci USA*, 2003; 100:15346-15351.

Lim et al., "Mechanism of Action of Bimatoprost, Latanoprost, and Travoprost in Healthy Subjects, A Cross Over Study," *Ophthalmology*, 2008; 115:790-795.

Liu et al., "Collagen-phosphorylcholine interpenetrating network hydrogels as corneal substitutes," *Biomaterials*, Mar. 2009; 30(8):1551-1559.

Liu et al., "A Simple Cross-Linked Collagen Tissue Substitute for Corneal Transplantation," *Invest. Ophthalmol. Vis. Sci.*, 2006; 47:1869-1875.

Liu et al., "Glucose permeable poly (dimethyl siloxane) poly (N-isopropyl acrylamide) interpenetrating networks as ophthalmic biomaterials," *Biomaterials*, Jan. 2005; 26(3):233-244.

Liu et al., "Trehalose loading through the mitochondrial permeability transition pore enhances desiccation tolerance in rat liver mitochondria," *Biochimica et Biophysica Acta.*, Nov. 2005; 1717(1):21-26.

Lohmann et al., "Corneal Haze after Excimer Laser Refractive Surgery: Objective Measurements and Functional Implications," *European Journal of Ophthalmology*, 1991; 1:173-80.

Ma et al., "Repeat penetrating keratoplasty versus the Boston keratoprosthesis in graft failure," *International Ophthalmology Clinics*, 2005; 45:49-59.

Ma et al., "Increased Platelet-Activating Factor Receptor Gene Expression by Corneal Epithelial Wound Healing," *Invest. Ophthalmol. Vis. Sci.*, 2000; 41:1696-702.

Mader et al., "Ocular and ocular adnexal injuries treated by United States military ophthalmologists during Operations Desert Shield and Desert Storm," *Ophthalmology*, 1993; 100:1462-7.

Marks, "An Improved Glucose-Oxidase Method for Determining Blood, C.S.F. and Urine Glucose Level," *Clinic Chimica Acta*, 1959; 4:19-24.

Mata et al., "Experimental Study of Diffusion Based Extraction form a Cell Suspension," *Microfluid Nanofluid*, Oct. 2008; 5:529-540.

Maus et al., "Comparison of Dorzolamide and Acetazolamide as Suppressors of Aqueous Humor Flow in Humans," *Arch Ophthalmol*, Jan. 1997; 115:45-459.

Maus et al., "The Effects of Sleep on Circulating Catecholamines and Aqueous Flow in Human Subjects," *Exp Eye Res.*, 1996; 62:351-358.

McLaren et al., "Standardization of corneal haze measurement in confocal microscopy," *Investigative Ophthalmology & Visual Science*, Nov. 2010; 51(11):5610-5616. Available online Jun. 10, 2010.

McLaren et al., "Automated Assessment of Keratocyte Density in Clinical Confocal Microscopy of the Corneal Stroma," *J Microsc.*, 2008; 229:21-31.

McLaren et al., "Measuring Corneal Thickness with the ConfoScan 4 and Zring Adapter," *Eye Contact Lens*, 2007; 33:185-190.

McLaren et al., "Corneal Thickness Measurement With the ConfoScan 4 Confocal Microscope and Z-Ring Adapter, and the Tandem Scanning Confocal Microscope," Abstract No. 1344, *Invest. Ophthalmol. Vis. Sci*, 2006; 47.

McLaren et al., "Keratocyte Density: Comparison of two Confocal Microscopes," *Eye and Contact Lens: Sci Clin Prac.*, 2005; 31:28-33.

McLaren et al., "Corneal Thickness Measurement by Confocal Microscopy, Ultrasound, and Scanning Slit Methods," *American J of Ophthalmology*, 2004; 137:1011-1020.

McLaren et al., "Effect of Ibopamine on Aqueous Humor Production of Normotensive Humans," *Invest Ophthalmol Vis Sci.*, 2003; 44:4853-4858.

McLaren et al., "Pupillometry in Clinically Sleepy Patients," *Sleep Med*, 2002; 3:347-352.

McLaren et al., "Comparison of Effects of Topical Ibopamine and Epinephrine on the Circadian Rhythm of Intraocular Pressure of the Rabbit Eye as Measured by Telemetry," *J. Ocular Pharm. Ther.*, 1999; 15(2):107-116.

McLaren et al., "A New Video Pachometer," *Invest. Ophthalmol. Vis. Sci*, 1999; 40:1593-1598.

McLaren et al., "Measuring Oxygen Tension in the Anterior Chamber of Rabbits," *Invest Opthalmol Vis Sci*, 1998; 39(10):1899-1909.

McLaren et al., "Continuous Measurement of Intraocular Pressure in Rabbits by Telemetry," *Invest Opthalmol Vis Sci*, 1996; 37:966-975.

McLaren et al., "Measurement of Transmission of Ultraviolet and Visible Light in the Living Rabbit Cornea," *Current Eye Research*, 1996; 15:411-21.

McLaren et al., "New Video Pupillometer," *Optical Eng.*, Mar. 1995; 34:676-683.

McLaren et al., "A Simple Three Compartment-Model of Anterior Segment Kinetics," *Exp Eye Res*, 1993; 56:355-366.

McLaren et al., "Computerized Analysis of Pupillograms in Studies of Alertness," *Invest Ophthalmol Vis Sci.*, Mar. 1992; 33(3):671-676.

McLaren et al., "Rate of Flow of Aqueous Humor Determined from Measurements of Aqueous Flare," *Invest Opthalmol Vis Sci*, 1990; 31:339-346.

McLaren et al., "A Scanning Ocular Spectrofluorophotometer," *Invest Opthalmol Vis Sci*, 1988; 29:1285-1293.

McLaren et al., "Measurement of Fluorescein and Fluorescein Monoglucuronide in the Living Human Eye," *Current Eye Research*, 1986; 27:966-974.

McLaren et al., "A Two-Dimensional Scanning Ocular Fluorophotometer," *Invest Opthalmol Vis Sci*, 1985; 26:144-152.

McLaren et al., "Light Sources of Fluorescein Fluorophotometry," *Applied Optics*, Sep. 15, 1983; 22(18):2897-2905.

McNamara et al., "Corneal Function During Normal and High Serum Glucose Levels in Diabetes," *Invest Opthalmol Vis Sci.*, 1998; 39:3-17.

(56) References Cited

OTHER PUBLICATIONS

Menovsky et al., "Effect of the $CO^2$ milliwatt laser on tensile strength of microsutures," *Lasers in Surgery and Medicine*, 1997; 20(1):64-68. Available online Dec. 7, 1998.
Mian et al., "In Vivo Femtosecond Laser-Assisted Posterior Lamellar Keratoplasty in Rabbits," *Cornea*, Dec. 2006; 25(10):1205-1209.
Mitooka et al., "Keratocyte Density of Central human Cornea after Laser in Situ Keratomileusis (LASIK)," *Am. J. Opthalmol*, Mar. 2002; 133(3):307-314.
Miyashita et al., "Collagen-Immobilized Poly(vinyl alcohol) as an Artificial Cornea Scaffold that Supports a Stratified Corneal Epithelium," *J. Biomed. Mater Res. B Appl. Biomater*, 2006; 76:56-63.
Moller-Pedersen et al., "Confocal Microscopic Characterization of Wound Repair after Photorefractive Keratectomy," *Invest. Ophthalmol. Vis. Sci*, Mar. 1998; 39(3):487-501.
Moller-Pedersen et al., "Corneal haze development after PRK is regulated by volume of stromal tissue removal," *Cornea*, 1998; 17:627-639.
Muscat et al., "Repeatability and reproducibility of corneal thickness measurements by optical coherence tomography," *Investigative Ophthalmology & Visual Science*, 2002; 43(6):1791-1795.
Nelson et al., "In Vitro Comparison of Chen and Optisol-GS Medium for Human Corneal Storage," *Cornea*, 2000;19:782-787.
Nishimura et al., "Initial Endothelial Cell Density and Chronic Endothelial Loss Rate in Corneal Transplants with Late Endothelial Failure," *Ophthalmology*, 1999; 106:1962-1965.
Norris et al. "3-O-Methyl-D-Glucose Improves Desiccation Tolerance of Keratinocytes," *Tissue Engineering*, 2006; 12(7)1873-1879.
Ohan et al., "Synergistic Effects of Glucose and Ultraviolet Irradiation on the Physical Properties of Collagen," *J. Biomed. Mater. Res.*, 2002; 60:384-391.
Ohno et al., "Keratocyte Activation and Apoptosis in Transplanted Human Corneas in a Xenograft Model," *Investigative Ophthalmology and Visual Science*, 2002; 43:1025-31.
Ohno et al., "Comparison of Recording Systems and Analysis Methods in Specular Microscopy," *Cornea*, 1999; 18:416-423.
Ono et al., "Preparation of novel hollow fiber silica using collagen fibers as a template," *Chemistry Letters*, 1999; 6(6):475-476.
Orssengo et al., "Determination of the true intraocular pressure and modulus of elasticity of the human cornea in vivo," *Bulletin of Mathematical Biology*, May 1999; 61(3):551-572.
Orwin et al., "Biomechanical and Optical Characteristics of a Corneal Stromal Equivalent," *Journal of Biomechanical Engineering*, Aug. 2003: 125:439-444.
Orwin et al., "In Vitro Culture Characteristics of Corneal Epithelial, Endothelial, and Keratocyte Cells in a Native Collagen Matrix" *Tissue Eng*, 2000; 6(4):307-319.
Ousley et al., "Objective screening methods for prior refractive surgery in donor tissue," *Cornea*, 2002; 21:181-188.
Oyster et al., "The Cornea and the Sclera," *The Human Eye: Structure and Function*, Sunderland, MA: Sinauer Associates Inc., 1999; 325-371.
Parc et al., "Manifestations and Treatment of Ocular Syphilis during an Epidemic in France," *Sex Transm Dis*, Aug. 2007; 34:553-556.
Parc et al., "Optic Nerve Ischemia as a Complication of Dental Extraction: A Case Report," *J Fr Ophtalmol.*, 2004; 27:921-923.
Patel et al., "Human Corneal Endothelial Cell Transplantation in a Human Ex Vivo Model," *Invest. Ophthalmol. Vis. Sci.*, May 2009; 50:2123-2131.
Patel et al., "The Effect of Corneal Light Scatter on Vision After Descemet-Stripping with Endothelial Keratoplasty," *Arch. Ophthalmol, In Press*, Feb. 2009; 127(2):153-60.
Patel et al., "The Effect of Corneal Light Scatter on Vision After Penetrating Keratoplasty," *Am. J. Ophthalmol*, Dec. 2008; 146(6):913-919.
Patel et al., "Scattered Light and Visual Function in a Randomized Trial of Deep Lamellar Endothelial Keratoplasty and Penetrating Keratoplasty," *Am. J. Ophthalmol*, 2008; 145:97-105.

Patel et al., "Objective Measurement of Backscattered Light from the Anterior and Posterior Cornea in Vivo," *Invest. Ophthalmol. Vis. Sci.*, 2007; 48:166-172.
Patel et al., "Confocal Microscopy Changes in Epithelial and Stromal Thickness up to 7 Years After LASIK and Photorefractive Keratectomy for Myopia," *J. Refract Surg.*, Apr. 2007; 23:385-392.
Patel et al., "Femtosecond Laser Versus Mechanical Microkeratome for LASIK: A Randomized Controlled Study," *Ophthalmology*, 2007; 114(8):1482-1490.
Patel et al., "Keratocyte Density and Recovery of Subbasal Nerves After Penetrating Keratoplasty and in Late Endothelial Failure," *Arch Ophthalmol*, 2007; 125(12):1693-1698.
Patel et al., "Keratocyte and Subbasal Nerve Density After Penetrating Keratoplasty," *Trans Am Ophthalmol Soc.*, 2007; 105:180-190.
Patel et al., "Objective measurement of backscattered light from the anterior and posterior cornea in vivo," *Investigative Ophthalmology and Visual Science*, 2007; 48:166-172.
Patel et al., "Diabetes and Hypertension in Isolated Sixth Nerve Palsy: A Population-Based Study," *Ophthalmology*, 2005; 112:760-763.
Patel et al., "Corneal Endothelium and Postoperative Outcomes 15 Years After Penetrating Keratoplasty," *Am J. Ophthalmol*, 2005; 139:311-319.
Patel et al., "Incidence, Associations, and Evaluation of Sixth Nerve Palsy using a Population-Based Method," *Ophthalmology*, 2004; 111:369-375.
Patel et al., "Corneal Endothelium and Postoperative Outcomes 15 Years After Penetrating Keratoplasty," *Trans Am Ophthalmol Soc.*, 2004; 102:57-66.
Patel et al., "Iris and Anterior Chamber Involvement in Acute Lymphoblastic Leukemia," *J. Pediatr Hematol Oncol.*, Aug. 2003; 25:653-656.
Patel et al., "Aberrant Regeneration of Corneal Nerves after Laser in Situ Keratomileus," *J Cataract Refract Surg.*, Feb. 2003; 29:387-389.
Patel et al., "Confocal Microscopy in Vivo in Corneas of Long-Term Contact Lens Wearers," *Investigative Ophthalmology and Visual Science*, 2002; 43:995-1003.
Patel et al., "Normal Human Keratocyte Density and Corneal Thickness Measurement by Using Confocal Microscopy in Vivo," *Invest Ophthalmol. Vis. Sci.*, 2001; 42:333-339.
Patel et al., "Automated Quantification of Keratocyte Density by Using Confocal Microscopy in Vivo," *Investigative Ophthalmology and Visual Science*, 1999; 40:320-326.
Patel et al., "Refractive-index of the human corneal epithelium and stroma," *Journal of Refractive Surgery*, Mar. 1995; 11(2):100-105.
Pinsky et al., "A Microstructurally-Based Finite Element Model of the Incised Human Cornea," *J. Biomechanics*, Jan. 10, 1991; 24:907-922.
Raecker et al., "Long-term Keratometric Changes After Penetrating Keratoplasty for Keratoconus and Fuchs Endothelial Dystrophy," *Trans Am J. Ophthalmol*, 2008; 106:187-195.
Raecker et al., "Long-Term Keratometric Changes after Penetrating Keratoplasty for Keratoconus and Fuchs Endothelial Dystrophy," *Am. J. Ophthalmol.*, Feb. 2009; 147(2):227-233, available online Oct. 2008.
Ragoonanan et al., "Roles of Membrane Structure and Phase Transition on the Hypersomotic Stress Survival of Geobacter Sulfurreducens," *BBA Biomembranes*, 2008; 1778:2283-2290. Available online Jun. 14, 2008.
Ragoonanan et al., "Heterogeneity in Desiccated Solutions: Implications for Biostabilization," *Biophysical Journal*, 2008; 94(5):1-16.
Ragoonanan et al., "Protein Stabilization," *Transfusion Medicine and Hemotherapy*, 2007; 34:246-252.
Rieck et al., "Increased Endothelial Survival of Organ-Cultured Corneas Stored in FGF-2-Supplemented Serum-Free Medium," *Invest Ophthalmol. Vis. Sci.*, 2003; 44:3826-32.
Robertson et al., "Retinopathy from a Green Laser Pointer: A Clinicopathologic Study," *Arch Ophthalmol*, 2005; 123:629-633.

(56) References Cited

OTHER PUBLICATIONS

Salacinski et al., "Iodination of Proteins, Glycoproteins, and Peptides using a Solid-Phase Oxidizing Agent, 1,3,4,6-tetrachloro-3 alpha,6 alpha-diphenyl glycoluril (Iodogen)," *Anal Biochem.*, 1981; 117:136-46.

Schornack et al. "Jupiter Scleral Lenses in the management of Chronic Graft Versus Host Disease," *Eye Contact Lens*, 2008; 34:302-305.

Shah et al. "The Development of a Tissue-Engineered Cornea: Biomaterials and Culture Methods," *Pediatric Research*, 2008; 63:535-544.

Sit et al., "Circadian Variation of Aqueous Dynamics in Young Healthy Adults," *Invest. Ophthalmol. Vis. Sci.*, 2008; 49:1473-1479.

Smolin et al., "Corneal graft rejection associated with anterior iris adhesion: case report," *Annals of Ophthalmology*, 1978; 10:1603-1604.

Solano et al., "Keratometric Astigmatism after Suture Removal in Penetrating Keraplasty: Double Running versus Single Running Suture techniques," *Cornea*, Nov. 2003; 22:715-720.

Storrie-Lombardi et al., "Determining Glucose Levels from NIR Raman Spectra of Eyes," *NASA Tech Briefs*, Apr. 2000; 24(4):52-53.

Stroncek et al., "Retroviral Transduction and Expansion of Peripheral Blood Lymphocytes for the Treatment of Mucopolysaccharidosis Type II, Hunter's Syndrome," *Transfusion*, Apr. 1999; 39:343-350.

Stylianopoulos et al., "A Structural, Kinetic Model of Soft Tissue Thermomechanics," *Biophysical Journal*, 2008; 94(3):717-725.

Suuronen et al., "Functional innervation in tissue engineered models for in vitro study and testing purposes," *Toxicol Sci.*, 2004; 82:525-33.

Suuronen et al., "Innervated human corneal equivalents as in vitro models for nerve-target cell interactions," *FASEB J.*, 2004; 18(1):170-2.

Sweeney et al., "A comparison of biological coatings for the promotion of corneal epithelialization of synthetic surface in vivo," *Invest. Ophthalmol. Vis. Sci.*, 2003; 44:3301-9.

Sweeney et al., "Nutritional requirements of the corneal epithelium and anterior stroma: clinical findings," *Invest. Ophthalmol. Vis. Sci.*, 1998; 39:284-91.

Taarnhoj et al., "Calibration of Measurements in Vivo of Fluorescein in the Cornea," *Exp. Eye Res.*, 1990; 51:113-118.

Tan et al., "Future Directions in Lamellar Corneal Transplantation," *Cornea*, Oct. 2007; 26(Supplement):S21-S28.

Thach et al., "Severe eye injuries in the war in Iraq, 2003-2005," *Ophthalmology*, 2008; 115:377-82. Available online Sep. 27, 2007.

Thach et al., "Intraocular foreign body injuries during Operation Iraqi Freedom," *Ophthalmology*, 2005; 112:1829-33.

Van den Berg et al., "Light transmittance of the human cornea from 320 to 700 nm for different ages," *Vision Research*, Jun. 1994; 34(11):1453-1456.

Van Horn et al., "Regenerative capacity of the corneal endothelium in rabbit and cat, " *Invest. Ophthalmol. Vis. Sci.*, 1977; 16:597-613.

Walsh et al., "Fibre optic spectrophotometry for the in vitro evaluation of ultraviolet radiation (UVR) spectral transmittance of rabbit corneas," *Physiological Measurement*, Mar. 7, 2008; 29(3):375-388.

Wang et al., "An ultrasonic technique for the measurement of the elastic moduli of human cornea," *J. Biomech.*, Dec. 1996; 29(12):1633-1636.

Wiffen et al., "The Effect of Contact Lens Wear on the Central and Peripheral Corneal Endothelium," *Cornea*, 2000; 19:47-51.

World Health Organization, "Consultation Meeting on Transplantation with National Health Authorities in the Western Pacific Region," Meeting held in Manila, Philippines, Nov. 7-9, 2005. Report published Sep. 2006.

Xie et al., "A thin glycoprotein coating of a synthetic lenticule does not cause nutritional deficiency of the anterior cornea," *Current Eye Research*, 1999; 18:335-41.

Yarmush et al., "Hepatic tissue engineering: Development of Critical Technologies," *Ann NY Acad Sci.*, 1992; 665:238-252.

Ye et al., "Structure and Infrared Emissivity of Collagen/$SiO_2$ Composite," *Appl. Surface Sci.*, 2008; 254(18):5975-5980. Available online Apr. 9, 2008.

Younge et al., "Retinal Image Stability in Head Tremor and Nystagmus: Counterintuitive Observations," *J Neuro-Ophthalmol.*, 2007; 27(2):107-114.

Zeng et al., "A Comparison of Biomechanical Properties Between Human and Porcine Cornea," *J. Biomech*, 2001; 34:533-537.

Zieske, "Extracellar Matrix and Wound Healing," *Curr. Opin. Ophthalmol.*, 2001; 12:237-41.

\* cited by examiner

A: Bright Field

B: Fluorescence

C

D

A

B

C

D

A

B

C

D

A

B

C

D

SILICA-BASED COMPOSITE OCULAR DEVICE AND METHODS

CONTINUING APPLICATION DATA

This application is a U.S. National Stage Application of International Application No. PCT/US2011/024032, titled SILICA-BASED COMPOSITE OCULAR DEVICE AND METHODS, filed on Feb. 8, 2011, published in the English language on Aug. 11, 2011 as International Publication No. WO 2011/097619 A2, which claims the benefit of U.S. Provisional Patent Application Ser. No. 61/302,362, filed Feb. 8, 2010, each of which is incorporated by reference herein in its entirety.

BACKGROUND

The cornea is the most anterior portion of the eye and creates the interface between the eye and the external environment. Due to its location, the cornea acts as a barrier, shielding the inner eye from foreign debris. The cornea must also allow light to pass through to the lens and, ultimately, the retina. The cornea is responsible for a majority of the light refraction into the eye.

The cornea is a highly ordered tissue. FIG. 12 depicts the layers of the cornea: the epithelium, Bowman's layer, the stroma, Descemet's membrane, and the endothelium, from anterior to posterior. The epithelium is made up of six to eight layers of epithelial cells. The newest, youngest, cells are the most posterior and move up through the layers to the most anterior cornea. This makes the cells at the anterior cornea the oldest, and these are swept away in the tear film as they age (Oyster and Clyde, "The Cornea and the Sclera," in *The Human Eye: Structure and Function*. Sinauer Associates, Inc.: Sunderland, Mass.; 1999. Pages 325-371). At its thickest portion, the epithelium accounts for 10% of the total corneal thickness. The epithelium acts as a water barrier between the external environment (including tears) from the stroma (Id). The cornea is avascular, but the epithelium contains a large number of nerve endings that respond to pressure stimuli.

The cornea is repaired by limbal cells, which are epithelial progenitor cells (Id.). Limbal cells are located in the conjunctiva, as shown in FIG. 13. The cells migrate laterally from the conjunctiva to the cornea, where they differentiate into epithelial cells.

Bowman's layer connects the epithelium to the stroma. The stroma is made up of ordered layers of type I collagen that account for roughly 90% of the cornea (Id). Fibroblast cells, also known as keratocytes, inhabit and organize the layers of collagen. The stroma provides the structural and mechanical support that the cornea requires. It also helps maintain the proper shape for the refraction of light into the lens.

Binding the endothelium to the stroma is Descemet's membrane, a protein layer that acts as a basement membrane for the endothelium. It is roughly three to four micrometers thick, about the same as the endothelium (Id.). The endothelium is a very metabolically active layer between the aqueous and the stroma. It acts mainly as a water pump to keep the stroma dry, which maintains the clarity of the cornea (Id.).

The three cell types of the cornea (epithelial, fibroblast, and endothelial) can be isolated using techniques described by Orwin and Hubel (Orwin et al., 2000 Tissue Eng. 6:301-19). This technique involves mechanical removal of the endothelial cells, and removal of the fibroblast and epithelium using the proteins collagenase and dispase, respectively. Limbal cells can also be extracted using the knowledge that they readily migrate from the conjunctiva.

Millions of patients worldwide are afflicted by corneal blindness. Failure of the cornea can result from various pathologies (keratoconus, Fuchs' dystrophy, post-cataract surgery complications, trauma, infection, etc.), and contributes significantly to morbidity and disability. Additionally, in the battlefield, combat injuries to the head and neck outnumber torso injuries by nearly 4 to 1. The eyes (and surrounding orbit) are the most frequently injured regions of the soldier's head and neck (Miyashita et al., 2006 J. Biomed. Mater. Res. B Appl. Biomater 76:56-63; Doillon et al., 2003 Int. J. Artif. Organs 26:764-73; Duan and Sheardown, 2006 Biomaterials 27:4608-17; Bryans et al., 2000 J. Sol-Gel SciTech 17:211-217). These injuries are significant sources of morbidity and mortality in fighting troops.

The cornea is a complex and unique tissue that is avascular and is predominantly composed of extremely ordered collagen lamellae. The purpose of the cornea is to refract light and transmit it to the retina. For optimal function, the cornea must be transparent (Freund et al., 1986 J. Optical Soc. Am. 3:1970-1982). In addition, the cornea is a connective tissue that must withstand intraocular pressure, the normal range of which is 10-21 mm Hg (Pinsky and Datye, 1991 J. Biomechanics 24:907-922), and constantly changing environmental conditions (ambient temperature, pH of the tear fluid, ultraviolet (UV) exposure, exposure to chemical fumes, dust, etc.). The biomechanical characteristics of the cornea are also very important.

Corneal transplants are commonly used to treat corneal disease and injury. Indeed, the cornea is the most commonly transplanted tissue in the United States with over 46,000 transplants performed annually (EBAA, "EBAA releases 2004 statistical report on eye banking. Washington DS: Eye Bank of America," 2005:1-2). The worldwide demand for corneal tissue suitable for transplantation, however, cannot be met by the supply (generally, a total of 120,000 transplants are available for 10,000,000 patients, as reported by the World Health Organization (Consultation Meeting on Transplantation with National Health Authorities in the Western Pacific Region: World Health Organization, 2005)), and a similar situation may present itself in United States in the next few years (Eglin et al., 2005 Biomed. Mater. Eng. 15:43-50; Freund et al., 1986 J. Optical Soc. Am. 3:1970-1982; Pinsky and Datye, 1991 J. Biomechanics 24:907-922; Buzard, 1992 Refract. Corneal Surg. 8:127-38; Shah et al., 2008 Pediatric Research 63:535-544).

In order to address the pressing need for corneal implants, medical researchers have turned to corneal substitutes. However, the combination of strength and transparency of the cornea is unique, and represents a significant challenge when recreating this tissue in vitro. Synthetic corneal substitutes (keratoprostheses) are used to a limited extent in clinical practice. Current indications for keratoprostheses include corneal scarring from severe ocular surface disorders, and multiple failed corneal transplants. However, artificial corneas in current use, including those made of either polymethylmethacrylate (PMMA) or poly(2-hydroxyethylmethacrylate) (pHEMA), do not bio-integrate with surrounding tissues, nor do they allow epithelialization of their surface. Keratoprostheses made of pHEMA have a porous skirt to promote bio-integration, but neither true biointegration nor epithelialization of the prosthesis surface occurs. Consequently, complications such as host tissue melting, extrusion, and intraocular infection are common (Eglin et al., 2006 J. Mat. Chem. 16:2220-2230; Heinmann et al., 2007 Adv. Engr. Mats. 9:1061-1068). There is, therefore, tremendous interest for developing a tissue-engineered cornea (Lang et al., 1981 Current Eye Research 1:161-7; Liu et al., 2006 Invest. Ophthalmol. Vis. Sci. 47:1869-1875; Kelley et al., 1984 Invest. Ophthalmol. Vis. Sci. 25:1061-4; Balm et al., 1982 Ophthalmology 89:687-99; Evans et al., 2002 Biomaterials 23:1359-67; Ma and Bazan, 2000 Invest. Ophthalmol. Vis. Sci. 41:1696-702).

SUMMARY OF THE INVENTION

Existing artificial corneas suffer from sub-par mechanical properties (approximately an order of magnitude less strength than those of the native tissue), difficulty in surgery (most cannot easily be sutured due to mechanical property mismatch) and poor biocompatibility (lack of epithelialization).

The present invention is drawn to biocompatible ocular devices for medical, veterinary or cosmetic use. The ocular devices of the present invention reflect improvements in all these characteristics. The ocular devices of the invention are based on the incorporation of organic materials (e.g., a fibrillar protein such as collagen and, optionally, basement membrane molecules such as laminin) that enable tissue and cell growth into a material (silica) known for its superior mechanical, optical, and biocompatibility properties. This creates a hybrid material, more specifically a biocompatible composite material foamed from silica and a fibrillar protein, that brings together the best of the two worlds: natural materials in a synthetic implant.

In one aspect, the invention includes a synthetic corneal implant fabricated from a composite material comprising silica and a fibrillar protein, together with methods of making and using the corneal implant. The fibrillar protein is preferably collagen, but other fibrillar proteins or peptides can be used. It should be understood therefore that wherever herein the ocular device is described as having a "collagen" component, such device can, in alternative embodiments, contain one or more other fibrillar proteins, either instead of or in addition to collagen. The corneal implant may take any desired shape or form; for example, it can be a complete, fully penetrating keratoprosthesis, a partial lamellar implant, or a more complex implant such as, for example, an implant that incorporates characteristics of both—e.g., penetration and partial thickness.

In another aspect, the invention includes a removable contact lens fabricated from a composite material comprising silica and a fibrillar protein, as well as methods of making and using the contact lens. The fibrillar protein is preferably collagen; once again, however, it should be emphasized that wherever herein the ocular device is described as having a collagen component, such a device can, in alternative embodiments, contain one or more other fibrillar proteins, either instead of or in addition to collagen. The contact lens can be fabricated for use in vision correction, cosmetics (e.g., eye color changes), as a drug delivery device, or as a protective device to protect the cornea such as, for example, as an ocular bandage during military combat or after an injury or surgery. As a therapeutic ocular device, the contact lens can provide relief from ocular pain, promote corneal healing, provide mechanical protection and support, maintain corneal epithelial hydration, and be used to deliver drugs. The ocular device can contain therapeutic agents intercalated into the pores or otherwise dispersed within the lens, or covalently or noncovalently bonded to the structure.

It should be understood that any and all features of the invention recited herein, including but not limited to various individual components of the silica/collagen composite material, various parameters concerning device structure, methods of use, and the like, whether or not said components or features are recited together in the context of one embodiment or recited in different passages herein with respect to different embodiments, can be combined together in any combination to form the novel ocular device or method as envisioned by the invention.

BRIEF DESCRIPTION OF THE FIGURES

FIG. 2 shows samples of collagen/TMOS composite artificial cornea constructs produced.

FIG. 6 shows transparency values for silica, collagen and hybrid composites at the two ends of visible light spectra. The data values at 400 nm and 700 nm were shown for clarity.

DETAILED DESCRIPTION

Figure 1:
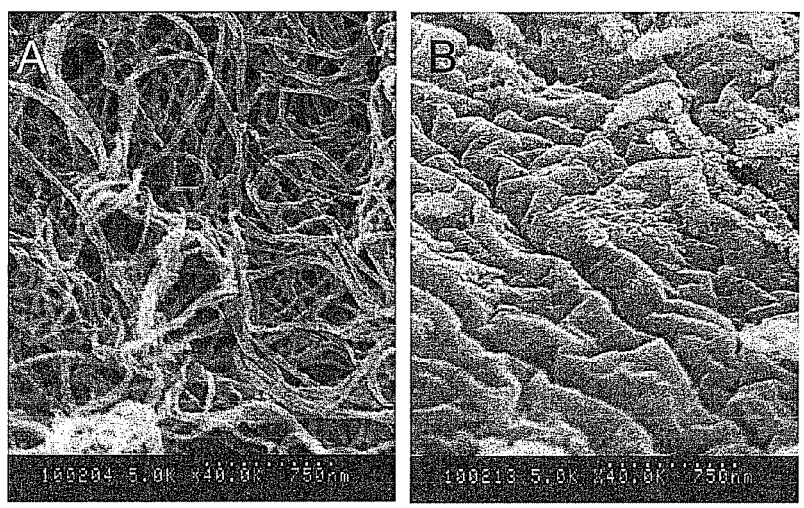
FIG. 1 shows a scanning electron micrograph of (a) collagen gel; (b) collagen/silica hybrid matrix.

The silica/collagen hybrid material, also referred to herein as a matrix or a composite, that is used for fabricating the articles of the invention includes a silica component and a fibrillar, preferably collagen, component. In this regard it should be understood that references to a "silica/collagen" composite herein should be broadly and generally understood to include a composite made from a silica gel or sol (e.g., a hydrolyzed silica precursor), and a fibrillar component as described in more detail below, typically collagen. The hybrid material can be formulated so that it is mechanically strong, supportive of cell growth, and moldable. In some cases, the hybrid material may be sterilizable and/or capable of being manufactured aseptically.

Silica is found in many simple life forms such as diatoms, which are transparent. These organisms also use silica to provide structural rigidity (Avnir et al., 2006 J. Materials Chemistry 16:1013-1030). Thus, silica in nature provides both optical transparency and strength. These intrinsic properties combined with favorable chemistry have made silica gels attractive for biotechnology applications. Silica gels are formed through hydrolysis of precursors such as, for example, tetramethoxysilane (TMOS), tetraethoxysilane (TEOS), methyltriethoxysilane (MTMOS) etc. to produce meso-/nano-porous matrices (the gel), which may include branched or unbranched, cross-linked or non-crosslinked, siloxanes. Porosity of the gel can be adjusted by adding osmolytes such as polyols, salts and sugars into the solution (the sol). The gels can also be easily functionalized to have different surface characteristics, and they can be manufactured practically in any shape. By changing the density, shape, and connectivity of the pores, the mechanical properties of the gel can be controlled to produce gels that have higher stiffness or toughness. By adjusting the processing conditions such as the temperature, pH, and relative humidity of the environment, the degree of connectivity of the pores can also be engineered. With time and storage conditions, the gel continues to age, reaching its steady state value within 72 hours under most conditions. A variety of techniques such as, for example, Raman spectroscopy, FTIR spectroscopy, atomic force microscopy, scanning electron microscopy, and transmission electron microscopy can be utilized to characterize gels made from different precursors under different conditions (Bryans et al., 2000 J. Sol-Gel SciTech 17:211-217).

Another area of recent interest is silica-induced collagen self-assembly (Eglin et al., 2005 Biomed. Mater. Eng. 15:43-50). Different silica precursors can change the hydrogen-bonding network of water in their close proximity. Thus, silica-induced changes in water structure can promote collagen self-assembly. The assembly kinetics and the resulting fiber characteristics are influenced by the chemical characteristics of the silica precursors and the processing conditions (Eglin et al., 2006 J. Mat. Chem. 16:2220-2230). Once the soft self-assembled structures are formed, the silica network gels, forming a hard cast and "locking" the final geometry peiivanently.

An ocular device fabricated from the silica/collagen hybrid material of the invention can serve as an effective corneal replacement. Transparency of the silica-based corneal replacement can equal that of the native cornea—although in some applications, transparency may not necessarily be a requirement, corneal cells can readily migrate across and/or attach to the surface, and biomechanical properties can be modulated.

An ocular device fabricated from the silica/collagen hybrid material of the invention can also serve as a contact lens. The mechanical strength of the composite material, coupled with its optical transparency and biocompatibility, make the composite material well-suited for this application as well.

Fibrillar Component

The fibrillar component of the ocular article can include any of the proteins that comprise the principal structural proteins of the body, such as collagens, elastins, keratin, actin, and myosin. Preferably, however, the fibrillar component is a collagen component. It should be understood that when the ocular device is described herein as having a collagen component, such device can, in alternative embodiments, contain one or more other fibrillar proteins, either instead of or in addition to collagen. In a particularly preferred embodiment, the fibrillar component includes a soluble collagen, such as atelo- or tropocollagen. Tropocollagen is a twisted helix trimer, about 1.5 nm in diameter with teliopeptides present. Collagen fibrils are aggregates of tropocollagen, about 20 nm in diameter. Semi-crystalline collagen fibers are bundles of fibrils. Any collagen or collagen-like molecule can be advantageously utilized as the fibrillar component. The collagen may be crosslinked or non-crosslinked. When crosslinked, the crosslinking may be accomplished using any suitable method known and routine to those of ordinary skill in the art and can include, for example, UV-induced, dehydrothermal, or chemical crosslinking. Collagen also promotes pliability of the composite material.

In one example, thermally denatured collagen (gelatin) is used in the silica gel. Thus, collagen either in solubilized form or pre-treated (e.g., thermally or chemically) to induce crosslinking or denaturation can be used in the making of the silica gel. The thermal treatment conditions can include, for example, exposure to temperatures in excess of 60° C. for longer than two minutes. In a typical gel that incorporates denatured collagen, 4.8 mg/mL collagen solution may be exposed to 70° C. heat for five minutes and then is mixed with silica precursors for gelification.

The collagen may include any type, or any combinations of types, of collagen including, for example, type I (the most abundant form in the human body), type II, type III, type IV, type V, type VI, type VII type, VIII, type IX, type X, type XI, type XII, type XIII, type XIV, type XV, type XVI, type XVII, type XVIII, type XIX, type XX, type XXI, type XXII, type XIII, type XIV, type XXV, type XXVI, type XXVII, type XXVIII, or type XXIX collagen. The particular type of collagen selected may influence the mechanical properties and/or size of fibrils formed by the collagen. In certain embodiments, type I collagen may be preferred.

Another preferred fibrillar component includes cellulose or a derivative thereof, such as methyl cellulose. More particularly, cellulose or a cellulose derivative can be substituted, in whole or in part, for the collagen component in any embodiment of the composite material or ocular device of the invention.

In other embodiments, the fibrillar component can include, for example, a polypeptide such as, for example, elastin, keratin, actin, or myosin; a polysaccharide such as, for example, cellulose or chitin; an amyloid fiber, a glycosaminoglycan; a proteoglycan; or any combination of fibrillar components.

Silica Component

Silica is naturally occurring and biocompatible. Silica gels, which can be produced by hydrolysis of a silica precursor, have been shown to be chemically inert, non-toxic, and can be engineered to have specific properties (porosity, optical clarity, mechanical stiffness, etc.). In addition; silica gels can be easily and cheaply manufactured into different shapes. The optical and manufacturing properties of silica gels are so favorable that microscope lens manufacturers have started to manufacture lenses from this material. Silica gels are also an excellent matrix for immobilization of macromolecules (proteins, drugs, etc.). Furthermore, silica influences self-assembly of collagen in vivo and provides potential as a template for controlling on a molecular level the nanostructure of the resulting matrix (Eglin et al., 2005 Biomed. Mater. Eng. 15:43-50).

Exemplary precursors for the silica component of the composite material include those shown in Table 1. The composite material can include any, or any combination of two or more, of the silica precursors listed in Table 1.

TABLE 1

Exemplary Silica Precursors

| Chemical Name | Acronym | Molecular Formula |
|---|---|---|
| Tetramethylorthosilicate | TMOS | $Si(OCH_3)_4$ |
| Tetraethylorthosilicate | TEOS | $Si(OC_2H_5)_4$ |
| Tetrakis(2-hydroxyethyl)orthosilicate | THEOS | $Si(OCH_2CH_2OH)_4$ |
| Methyldiethoxysilane | MDES | $C_5H_{14}O_2Si$ |
| 3-(Glycidoxypropyl)triethoxysilane[1] | GPTES | $C_{12}H_{26}O_5Si$ |
| 3-(Glycidoxypropyl)trimethoxysilane[1] | GPTMS | $C_9H_{20}O_5Si$ |
| 3-(Trimethoxysilyl)propylacrylate | TMSPA | $H_2C=CHCO_2(CH_2)_3Si(OCH_3)_3$ |
| N-(3-Triethoxysilylpropyl)pyrrole | TESPP | |
| Vinyltriethoxysilane | VTES | $H_2C=CHSi(OC_2H_5)_3$ |
| Vinyltrimethoxysilane | VTMES | $H_2C=CHSi(OCH_3)_3$ |
| Methacryloxypropyltriethoxysilane | TESPM | |
| Silica Nanoparticles[1,2] | | $SiO_2$ |
| Sodium Silicate (e.g., 27% Silicic Acid 10% NaOH) | Water glass | |
| Diglycerylsilane[1] | DGS | |
| Methyltriethoxysilane[1] | MTMOS | $CH_3Si(OCH_3)_3$ |
| 3-aminopropyltriethoxysilane[1] | APTS | $H_2N(CH_2)_3Si(OC_2H_5)_3$ |
| 3-aminopropyltrimethoxysilane[1] | APTMS | $C_6H_{17}NO_3Si$ |
| 3-(2,4-Dinitrophenylamino)propyltriethoxysilane | | |
| Mercaptopropyltriethoxysilane | TEPMS | $HS(CH_2)_3Si(OCH_2CH_3)_3$ |
| 3-(2-Aminoethylamino)propyltriethoxysilane | | $(CH_3O)_3Si(CH_2)_3NHCH_2CH_2NH_2$ |
| Isocyanatopropyltriethoxysilane[1] | | $C_{10}H_{21}NO_4Si$ |
| Hydroxyl-terminated polydimethylsiloxane[1] | PDMS | |
| Triethoxysilyl-terminated polydimethylsiloxane[1] | PDMS | |
| Methyltriethoxysilane[1] | MTES | $CH_3Si(OC_2H_5)_3$ |
| Triethoxysilyl-terminated poly(oxypropylene) | | |

[1]Exemplary precursors that may function as plasticizers.
[2]e.g., LUDOX (W. R. Grace & Co., Columbia, MD), NYACOL (Nyacol nano Technologies, Inc., Ashland, MA), or CAB-O-SIL (Cabot Corp., Boston, MA)

The collagen component is preferably porcine collagen but may be collagen from other animal sources, including marine sources, or synthetic collagen. Natural or recombinant human collagen is also a preferred collagen.

In some embodiments, the silica/collagen hybrid material may be prepared using alkoxysilanes that produce an alcohol as a byproduct of hydrolysis, such as tetramethoxysilane (TMOS) (which produces methanol as a byproduct), tetraethoxysilane (TEOS) (which produces ethanol as a byproduct) tetrakis (2-hydroxy ethyl) orthosilicate (THEOS) (which produces ethylene glycol as a byproduct), as well as sodium silicate. Composites of the aforementioned silica materials with carbohydrates, e.g., polysaccharides, are also suitable for use as the silica component. In other embodiments, the silica component can include, for example, silica nanoparticles such as LUDOX (7 nm, 12 nm, or 22 nm particles with sodium ion as a counter ion bonded to the silica surface; W.R. Grace & Co.; Columbia, Md.), NEXSIL 85 and 125 (silica nanoparticles with sodium ion as a counterion; Nyacol Nano Technologies; Ashland, Mass.), NEXSIL 20K, 85K and 125K (20 nm, 50 nm, or 85 nm) (silica nanoparticles with potassium ion as a counterion; Nyacol Nano Technologies; Ashland, Mass.), and NEXSIL 20A, 45Z, 85A, 125A (20 nm, 35 nm, 50 nm, or 85 nm) (silica nanoparticles with no counterion; the surface charge is slightly negative; Nyacol Nano Technologies; Ashland, Mass.). In still other embodiments, a preferred silica precursor can include methyltriethoxysilane (MTMOS).

It should be understood that the invention is not limited to the particular silica precursor used, and that there are numerous silica precursors that have been and can be used to form silica gels (see Avnir et al., 2006 J. Materials Chemistry 16:1013-1030 for review), through various surface modification techniques, and which are suitable for use in the invention.

Silica/Collagen Composite

The silica precursor is typically hydrolyzed (e.g., by sonication) to faun a silica gel or "sol" (an un-solidified silica in liquid form) prior to mixing with the fibrillar component to yield the silica/collagen composite of the invention. Thus, the silica component is a liquid. The concentration of the silica component in the composite material depends on the nature of the silica component and the desired properties of the material. In embodiments of the ocular device employing TMOS as the silica component, exemplary concentrations of TMOS in the composite material can range from 20 mg/mL or less to 120 mg/mL or more, as shown in Example III.

The fibrillar component (e.g., collagen) also can be provided in liquid form as a solution. For example, a solution of about 1-20 mg/mL soluble collagen can conveniently be used as a starting material for formation of the composite material.

Collagen concentrations in the finished composite material typically range between about 1 mg/mL and about 10 mg/mL. Collagen concentration may be selected so as to permit the silica precursor to induce collagen self-assembly while still preserving its ability to loan a gel through hydrolysis. At collagen concentrations below about 1 mg/mL, the viscosity of the composite material may be too low; at collagen concentrations above about 10 mg/mL, the composite material may become too viscous to be easily manipulated.

The ratio of silica component to fibrillar component (referred to herein for convenience as the "silica/collagen" ratio, with the understanding that the fibrillar component is not limited to collagen) in the composite material of the invention, on a weigjht/weight basis, may range from 1:40 (w/w) or lower, to 40:1 (w/w) or higher, although it may be possible to produce suitable devices from composite material possessing a silica/collagen ratio outside of this range. Example III show experimental results for composite materials having silica/collagen ratios (w/w) of about 5:1, 11:1, 25:1 and 33:1 which composites are designated in Example III as "5/95," "10/90," "20/80" and "25/75," respectively.

The concentration of either or both the collagen component and the silica component can be readily varied to suit the particular purpose of the ocular device.

Exemplary silica/collagen ratios include, for example, 40:1, 35:1, 33:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:25, 1:30, 1:33, 1:35, and 1:40.

In certain contact lens embodiments, it may be advantageous to use a higher "silica/collagen" ratio than that used for certain corneal implants.

As noted elsewhere herein, the composite material may contain, in addition to the fibrillar component and the silica component, any number of additional optional components including one or more osmolytes, cytophilic biomolecules, plasticizers, therapeutic agents, buffers, salts, pharmaceutically acceptable reagents or carriers, and the like. Osmolytes, cytophilic biomolecules, plasticizers, therapeutic agents, buffers, salts, pharmaceutically acceptable reagents or carriers, are well known to the art and additionally are described in many of the documents cited herein.

Osmolytes

During manufacturing of the composite material, an osmolyte may be included in the reaction mixture to, for example, modulate collagen assembly, reduce matrix brittleness, and/or to adjust the matrix porosity, since selection of the osmolyte can influence the size of the pores. The osmolyte is preferably non-cytotoxic, biocompatible, non-reducible, and nonpolar. Preferred osmolytes include polyols and carbohydrate-based osmolytes including disaccharides and polysaccharides. Thus, exemplary preferred osmolytes can include, for example, trehalose and sucrose, dextran, glycine, and glycerol, which have the beneficial property that they can be easily washed off the matrix after gelation, if desired, and are also compatible with cells.

In some embodiments, the osmolyte may be an organic compound such as, for example, a polymer. Polymers such as, for example, polymethylmethacrylate (PMMA), polydimethylsilane (PDMS), or polyethylene glycol (PEG) may be desirable osmolytes in embodiments in which larger pore sizes are desired. In some of these embodiments, the silica precursor may be conjugated to the polymer. In some cases, manufacture of the device can include a silica/polymer-based intermediate that is not necessarily biocompatible, but subsequent production steps eliminate non-biocompatible functional groups, rendering the final device biocompatible.

Carbohydrate-based osmolyte concentrations in the reaction mixture are preferably in the range of 100 mM-700 mM. Polyols such as glycine and glycerol are preferably present at concentrations from 0-5% v/v based on total reaction volume. In some of the corneal implant embodiments or contact lens embodiments, the osmolyte may be omitted. In other embodiments, the osmolyte concentration can be adjusted to alter the porosity to control or enhance oxygen diffusion and/or drug release.

Surface Modification

Preferably, the corneal implant is not only biocompatible, but conducive to cell growth. It is therefore desirable that the composite material promote cell attachment and growth after implantation. To this end, one or more cytophilic biomolecules that promote cell attachment, such as laminin ("LN") or a polypeptide containing a subunit thereof (e.g., a YIGSR-containing peptide such as YIGSR (SEQ ID NO:1) or IKVAVYIGSR (SEQ ID NO:2)), or fibronectin or a polypeptide containing a subunit of fibronectin (e.g., an RGD-containing peptide), or a conjugate of a cytophilic molecule, are optionally introduced into or onto the composite matrix, thereby enhancing epithelialization. The cytophilic biomolecule is preferably a peptide containing at least five amino acids, more preferably at least 10 amino acids.

In one embodiment, the cytophilic biomolecule is adsorbed or coated onto the surface of the silica/collagen composite. An exemplary coating is about 1 microgram (μg) of cytophilic biomolecule, e.g. laminin, per $cm^2$. The amount of laminin peptide immobilized on collagen can be quantified by using peptides radiolabeled with $^{125}I$ and the Iodogen (1,3,4,6-tetrachloro-3α,6α-diphenyl glycoluril) method.

In another embodiment, the cytophilic biomolecule is covalently linked to a component of the composite, preferably but not necessarily the collagen component. In other embodiments, the silica molecules can be functionalized.

For example, collagen mimetic peptide (CMP; SEQ ID NO:3), which contains hydroxyproline and has the amino acid sequence -(Pro-Hyp-Gly)$_x$-, where x can be any number but is preferably 10, can be covalently linked to the cytophilic biomolecule to form a CMP conjugate. CMP is known to form a triple helix conformation that resembles the native protein structure of natural collagens. CMP has been shown to associate with type I collagen molecules and fibers via a strand invasion process, and can physically bind type I collagen when introduced in a denatured state. Particularly preferred CMP conjugates are (PHypG)$_{10}$-SGSGSG-YIGSR (SEQ ID NO:4) and (PHypG)$_{10}$-IKVAVYIGSR (SEQ ID NO:5). A flexible linker, such as (SG)$_3$ (SEQ ID NO:6), is optionally included in the conjugate to facilitate contact between the cytophilic biomolecules (e.g., peptides) and the cells.

The resulting CMP conjugate can be included as a fibrillar component during formation of the composite, or it can be introduced after composite formation. Alternatively, the CMP can be included as a fibrillar component, or introduced into the composite after formation, but prior to covalently linking the cytophilic biomolecule to the CMP molecule.

It should be understood that the invention is not limited to any particular method or means for including the cytophilic biomolecule in the corneal implant.

Biocompatibility of the corneal implant can be tested by implanting the device into animal and human corneas in an organ culture model ex vivo. Biocompatibility can be determined by examining re-epithelialization and stromal cell repopulation of the corneal substitute. The transparency of the corneal substitute in vivo can be assessed after implantation in a limited number of animal eyes.

Also, oxidation can alter the stability of the implant. Thus, in addition to modifying the surface to promote cell growth, the surface of the implant can be modified to reduce oxidation on the surface and, therefore, oxidation-associated changes in the implant. Such modifications can increase the stability of the implant. Such modifications include, for example, modifying silanol (Si—OH) groups that are hydrogen bonded with organic groups of the collagen (e.g., —NH2, —COOH, —OH, etc.). One alternative includes eliminating silanol groups of the surface by using a simple immersion technique in organic-terminated silanol solutions (e.g., R$_3$Si—NH$_2$, —COOH, —CH$_3$, —CH$_2$CH$_3$, etc.) that modify the surface of the device and promote cell adhesion.

Alternatively, one can react the surface of the composite with a polymeric coating that includes a natural polymer, a synthetic polymer, or a mixture of polymers, including a xture of natural and synthetic polymers. Exemplary suitable polymers include a low molecular weight PLL-PEG (poly (L-lysine)-polyethylene glycol) complex can be incorporated by a simple layer-by-layer deposition process. The silica surface carries a net negative electrical charge and promotes electrostatic interactions with positively charged lysine residues of PLL. Other methods of polymeric coatings also include spraying and plasma treatment.

Plasticizers

In some embodiments, one or more plasticizers may be incorporated into the silica/collagen hybrid material to provide flexibility and/or ductility to the matrix. Exemplary plasticizers include, for example, simple polyols. In some embodiments, the plasticizer can include one or more of the silica precursors identified in Table 1 as being a plasticizer including, for example, precursors that possess a non-hydrolyzable organic group.

Manufacture of the Ocular Device

The ocular device is manufactured using techniques in common use in the art for manufacture of medical devices from polymer composites. The silica gel/collagen composite is foamed by silica-induced collagen self-assembly and sol-gel hydrolysis. Preferably, hydrolysis is carried out by sonication to form the sol. The resulting composite material can be shaped, molded, extruded, spin-cast, lathe-cut or otherwise manipulated to form ocular device, which can take the shape of a disc, a dome, an annulus, a cylinder, or any other convenient shape. The manufacturing process can be adjusted to control the size and thickness of the device. Manufacturing processes suitable for use in fabricating the ocular devices of the invention are well known to the art and are exemplified in U.S. Pat. Nos. 4,676,790; 5,433,745; 7,364,674; 6,976,997; 6,814,755; 6,755,858; 6,508,837; 6,106,552; 6,005,160; 5,843,185; 5,836,313; 5,354,332; 4,470,159, and 6,897,271.

The diameter of the ocular device is selected with regard to the function to be performed and the patient whom is to receive it. Typically, the diameter of the ocular device is between 8 mm and 13 mm, although a partial implant may have a smaller diameter. The ocular device may possess uniform thickness, or the perimeter may be thicker or thinner than the central region of the device. The thickness of the implant may vary radially. For example, veterinary applications of this technology may involve implants having relatively larger diameters and thicknesses.

The corneal implant is structured so that it may be surgically attached in or on the cornea of a mammalian eye. As such it may optionally include, around the central region, an annular outer skirt of porous material to facilitate attachment and cell growth. In this embodiment, the outer skirt, which forms the perimeter of the device, is preferably more porous than the central region. The contact lens embodiment, on the other hand, is structured to be readily removable.

The ocular device may take any desired shape or form such as, for example, it can be a complete, fully penetrating keratoprosthesis, a partial lamellar implant, or a more complex implant such as, for example, an implant that incorporates characteristics of both—e.g., penetration and partial thickness. In such embodiments, a central region can extend from the bottom of the epithelial layer of the cornea to the top of the endothelial layer of the cornea, while the periphery of the ocular device may form a lamellar implant.

Optionally, the ocular device of the invention may be surface-modified at its rear (posterior) surface, or its front (anterior or external) surface, for example by covalent linkage of an activating group. For example, a functional group that can serve as a site for covalent or non-covalent linkage of a molecule of interest may be incorporated into the surface of the device.

Characteristics of the Ocular Device

With respect to the optical transparency, parameters that may affect transparency and light scattering include, for example, the diameter of the collagen fibrils, the spacing between the collagen fibrils, and/or the directionality or ordering of the collagen fibrils. In some embodiments, transparency of the ocular device is preferably >94% at 400 nm and >97% at 700 nm.

In certain embodiments such as, for example, an ocular bandage, however, transparency may be less of a consideration. Such embodiments may emphasize, for example, drug delivery over transparency since the device may be intended to be in place for a limited time during which a temporary reduction in, or a complete obstruction of vision may acceptable. Such circumstances can include, for example, hospitalization.

Mechanical strength of the composite material is affected by collagen and silica concentration, as well as post-condensation aging conditions such as the resultant water content (drying), aging temperature, pressure, relative humidity, etc. In the Examples below, the 20/80 TMOS/Tropocollagen composite showed similar stress/strain to native cornea.

In some embodiments, the ocular device may be aged using a wet aging procedure. In dry aging, the gel is initially kept in a low relative humidity (RH) environment (such as 0-10% RH) for 4-6 hours and then immersed in water where the aging process is continued for an additional 36 hours. In contrast, wet aging involves placing the gel in water for up to 48 hours and then used.

In certain embodiments, the microstructure of the composite material preferably may be nanoporous, and can be readily engineered to achieve the desired topography and porosity. In other embodiments such as, for example, where cell infiltration may be desirable to promote integration into host tissue, macroporous materials may be preferred.

EXAMPLES

The present invention is illustrated by the following examples. It is to be understood that the particular examples, materials, amounts, and procedures are to be interpreted broadly in accordance with the scope and spirit of the invention as set forth herein.

Example I

Collagen/silica Construct Manufacture and Characterization

A. Manufacture of Collagen/Silica Construct

Three different systems have been studied: collagen gels, TMOS gels and collagen/TMOS hybrids (also referred to herein as constructs, composites, biocomposites or matrices). Collagen gels were formed from soluble, lyophilized bovine type I collagen (Elastin Products Corporation; Owensville, Mo.). The collagen was dissolved in 0.005 M acetic acid at 2 mg/mL, 5 mg/mL, 7.5 mg/mL, or 10 mg/mL. The collagen solution was then neutralized to pH 7 by adding 1N NaOH and placed into an incubator at 37° C. Because of its ability to form gels quickly, even at pH 3, TMOS was used as the basis for the construct. TMOS solution was prepared from a volume ratio of $1:1:0.1 \times 10^{-3}$ of TMOS:Distilled Water:0.01 M HCl (i.e. 1 mL TMOS, 1 mL distilled water, 100 µl of HCl). The TMOS solution was then allowed to gel overnight, or neutralized to pH 7 with NaOH. Reactions were performed in a controlled humidity environment. Constructs were formed by mixing the collagen and TMOS solutions using a range of volume fraction ratios (0-20%). The solution was then allowed to gel overnight without adjustment of pH (FIG. 1). It is noteworthy that the construct is distinct in its structure from that of either of the base materials. These differences can be seen in scanning electron micrographs. These images suggest that the two components interact and influence self-assembly.

B. Characterization of Construct Properties

Figure 2A:
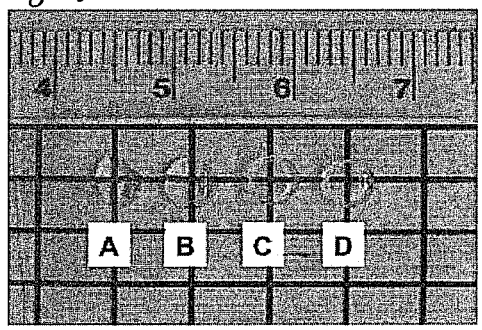
FIG. 2A shows sample A, 5 mg/mL pure collage; sample B, 10 mg/mL pure collagen; sample C, 2 mg/mL pure collagen+10% TMOS; and sample D, 5 mg/mL pure collagen+10% TMOS.
Figure 2B:
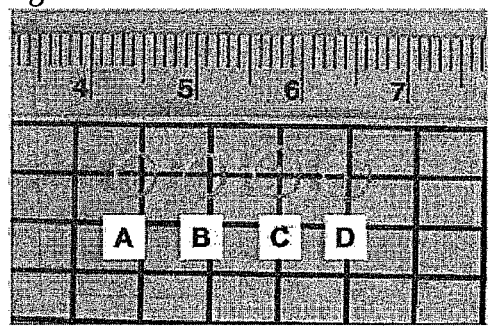
FIG. 2B shows sample A, pure TMOS; sample B, 10% trehalose+90% TMOS; sample C, 10% dextran+90% TMOS; and sample D, 10% glycerol+90% TMOS.
Figure 3:
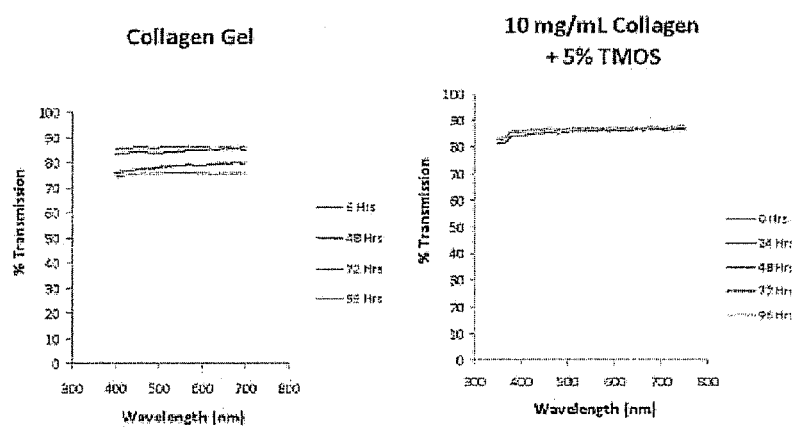
FIG. 3 shows transmittance of collagen gel and the construct as a function of wavelength and time post reconstitution.

Transparency. The basic optical properties of the construct can be seen using conventional photography (FIG. 2). The construct is transparent but modification of construct composition can influence its transparency. In order to quantify the influence of composition on optical characteristics, constructs of various compositions were examined through the visible spectrum (350 nm-750 nm) by using a spectrometer. Changes in the optical properties of the constructs were monitored for up to 5 days (FIG. 3). As seen below, by adjusting the relative concentrations of collagen and silica in the construct it is indeed possible to make constructs with optical properties as good as collagen gels with higher aging stability (compare the collagen gel spectra in FIG. 3 to the spectra obtained for 10 mg/mL collagen+5% TMOS). Specifically, the transmittance of a 10 mg/mL collagen+10% TMOS gel was approximately 90% after four days of aging. The transmittance of the native cornea ranges between 90-98% over the visible spectrum (Farrell et al., 1973 J. Physiology 233:589-612). These results demonstrate that the construct can exhibit favorable optical properties and that the properties can be modulated by varying the composition and method of manufacture.

Mechanical properties. We have performed preliminary unconfined compression testing of different constructs and these results are shown in Example III.

C. Cell Isolation and Culture

Donor cornea tissue, not suitable for transplantation, was used with human subjects' approval.

Epithelial cells: The limbus was removed and epithelial progenitor cells were obtained from those tissue explants. Small limbal segments were placed epithelial side down in a 6-well culture dish and allowed to dry for one hour. A small amount of epithelial media (Keratinocyte Growth Medium, EGF, Bovine Pituitary Extract, Insulin, and Hydrocortisone) was added to cover the segments and they were incubated overnight. Cell phenotype was determined by immunohistochemistry for the cytokeratin AE1/AE3 as pan-epithelial markers. All cells stained positive indicating epithelial origin.

Corneal fibroblasts were isolated by previously described methods. Briefly, the endothelial surface was removed by gentle swabbing. The remaining cornea was then cut into four sections and placed in a Dispase II solution at 4° C. to allow the solution to penetrate, then at 37° C. to dislodge the epithelial layers. The stromal segments were then placed in a collagenase solution for 15 minutes to remove any excess epithelial cells, followed by 30 minutes in collagenase to release stromal fibroblasts from the matrix. The collagenase solution was filtered through 40 µm filters and spun to obtain cells. Stromal fibroblasts were then plated in fibroblast media (DMEM: F12, 10% FBS, 1% ABAM, 0.1% Gentimycin).

D. Cell Attachment

Figure 4:
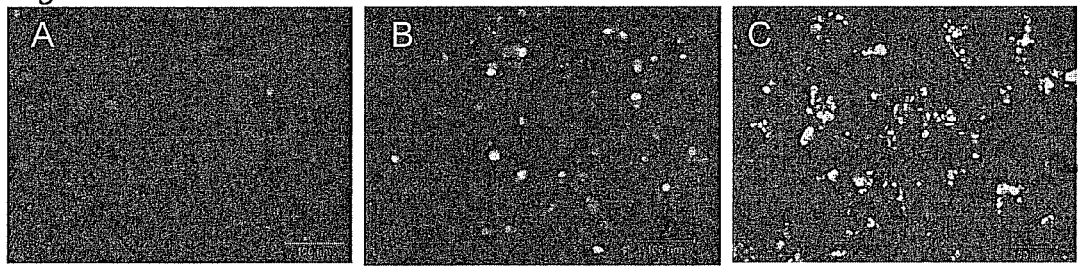
FIG. 4 shows human stromal fibroblasts seeded on the surface of the construct (a) unmodified; (b) coated with laminin; (c) coated with YSGIR peptide. Cells were permitted to attach for one hour and stained with acridine orange and imaged using fluorescent microscopy to improve contrast.

Basic biocompatibility of the construct was studied by seeding either stromal fibroblasts or co-culturing limbal segments from human donors on the surface and observing attachment, migration and morphology of the cells. Stromal fibroblasts were seeded on the surface of the construct and attachment of the cells at one hour was quantified. The surface of the construct was also modified by the adsorption of either laminin ("LN") or laminin-derived peptide, YIGSR (SEQ ID NO:1). The percentage of cells seeded on the surface that attached was quantified by removing the supernatant and counting the number of cells that had not attached (Table 2). These results demonstrate that attachment of the construct is high (~70%) and can be increased further through surface modification to >90%. Fluorescent micrographs of the stromal fibroblasts on the surface demonstrated that cells attach to the surface of the construct readily (FIG. 4). The cells seeded on the YIGSR (SEQ ID NO:1) modified surface have a slightly different morphology from those of the other surface. It is noteworthy that cells and construct have been co-cultured for weeks and stromal cell attachment and viability is maintained over the duration studied (data not shown).

TABLE 2

Attachment of stromal fibroblasts as a function of surface composition. Attachment was quantified after one hour of incubation.

| Surface Composition | % Attachment |
|---|---|
| Construct | 69 ± 14 |
| Construct + LN | 96 ± 1 |
| Construct + YIGSR | 98 ± 1 |
| Control* | 94 ± 9 |

*tissue culture treated plastic

Figure 5:
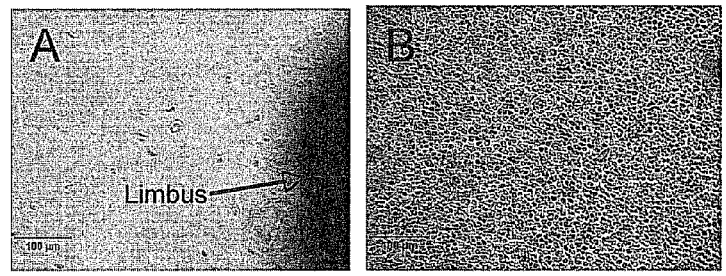
FIG. 5 shows outgrowth of human limbal epithelial cells onto the construct for (a) day 0; and (b) day 5 of culture. By day 5 there is extensive outgrowth of epithelial cells onto the surface of the construct.

Compatibility of the construct with epithelial cells is also important. In vivo, epithelial cells typically migrate from the limbal regions to cover the central cornea. In assessing the biocompatibility of the construct, we chose to examine the migration of epithelial cells from a limbal segment as a measure of compatibility of the construct. As with the stromal fibroblasts, epithelial cells attached readily to the construct and over a 5-day period, migrated extensively away from the limbal segment (FIG. 5). Surface modification of the hybrid (LN or YIGSR (SEQ ID NO:1)) improved the rate of migration and coverage of the matrix with epithelial cells.

These studies demonstrated that both epithelial and stromal fibroblasts cells readily attach to the surface of the hybrid matrix.

Example II

Optical and the Biomechanical Properties of the Artificial Corneal Construct

A more systematic understanding of the ultrastructure of the construct and its properties can be developed by analyzing the role of the composition, the manufacturing method, and aging on the biomechanical and optical properties of the construct. These parameters can also be evaluated for their impact on attachment and migration of corneal cells on the construct, and allow refinement of the design parameters for the construct.

A. Construct Compositions

The construct contains three different components: silica gel precursor, collagen, and the osmolyte. These components can be varied over a range of compositions.

Compositional Components

Collagen. Collagen concentrations are varied between 3-10 mg/mL. This range of collagen concentrations ensures that the silica precursor can induce collagen self-assembly while still preserving its ability to form a gel through hydrolysis. Collagen from marine sources or human recombinant sources may also be studied.

Silica precursors. Tetramethoxysilane (TMOS), tetraethoxysilane (TEOS), LUDOX (W. R. Grace & Co., Columbia, Md.), and sodium silicate are used as silica precursors.

Osmolyte. Certain polyol and carbohydrate-based osmolytes are used in the manufacturing of the matrix material to modulate collagen-assembly, reduce matrix brittleness, and to adjust the matrix porosity. We use common osmolytes such as trehalose, sucrose, dextran, glycine, and glycerol since they can be easily washed off the matrix after gelation and they are also compatible with cells. Carbohydrate osmolytes are evaluated in the range of 100-700 mM. Polyols such as glycine and glycerol are evaluated in concentrations from 0-5% v/v.

The sol is prepared and gelled at different processing conditions (time, temperature, pH, environmental hydration can be varied) to allow for self-assembly, homogeneous mixing, and hydrolysis. The gel is vacuum dried or spin dried and stored for 12-24 hours. Biomechanical properties and optical properties of the gel can are evaluated as described below.

Biomechanical property determination. Biomechanical properties of the artificial corneal construct are important for its success. These include the abilities a) to withstand intraocular pressure and stresses imposed on the globe, b) to match compliance with the surrounding stroma, and c) to facilitate suturing and attachment of the construct to the surrounding tissue during surgery.

Basic uniaxial tensile testing is conducted with dog-bone shaped samples while the compressive testing is conducted with cylindrical samples. Biomechanical characterization with samples that are manufactured in the exact dimensions of the cornea are also performed. These evaluations involve measuring stress relaxation and creep response of the construct as well as microindentation, biaxial tensile testing, and the suture pull-out tests as a function of hydration and during aging.

Optical property determination. The optical properties of the construct also vary depending on the composition (the type of silica and collagen used, or the presence of doping chemicals), and the structure of the construct. The optical transmittance of the samples through the visible spectrum (350-750 nm) are measured by using a spectrometer.

Outcome Evaluation. For compositions in which the transparency is greater than 94% (at 400 nm) and 97% (at 700 nm), biomechanical tests are performed. Specifically, ultimate tensile strength (UTS) and tensile modulus should be within one order of magnitude from native values. UTS for the native cornea is ~4 MPA (Bryant et al., 1994 Invest. Ophthalmol. Vis. Sci. 35:3022-31; Zeng et al., 2001 J. Biomech. 34:533-7) and ~8 MPA for the tensile modulus (Zeng et al., 2001 J. Biomech. 34:533-7; Ethier et al., 2004 Ann. Rev. Biomed. Eng. 6:249-73). Other investigators have engineered silica gels to result in tensile properties that span this range (0.01-10 GPa; Avnir et al., 2006 J. Materials Chemistry 16:1013-1030).

B. Manufacturing Process

A range of compositions (collagen, silica precursor, and osmolyte content) that result in the optical and biomechanical properties of interest are readily identified using the above procedures. The ultrastructure of the construct is examined to obtain more information on the effects of the composition and manufacturing techniques. In addition, samples are spin-dried to see if this methodology can be used to further strengthen the gel. This information permits manufacturing of artificial corneal scaffolds of homogeneous composition, uniform porosity, and strict geometric requirements for penetrating and lamellar artificial corneal constructs.

Microstructural characterization. Fourier-Transform Infrared (FTIR) and Raman Spectroscopy analyses are conducted pre-gelation with combinations of collagen and silica precursors in the presence of different osmolytes allowing evaluation of a) the uniformity of collagen distribution in the sol, and b) the changes in the structure and self-assembly kinetics of the collagen at different processing temperatures (in a range of 0° C. to 40° C.) and degrees of hydration. These evaluations help distinguish between the silica precursor-induced self-assembly and the aggregation of collagen during gelation. Ultrastructure of the gel (pore size and structure as well as the self-assembled structure hierarchy) is quantified using Scanning Electron Microscopy (SEM), Atomic Force Microscopy (AFM), and Confocal Raman Spectroscopy.

C. Aging

It is desirable that the constructs not exhibit significant changes in properties with exposure to different pH environments or UV exposure. Changes in the properties of the construct with time in culture (e.g. aging) are evaluated in vitro using constructs cultured with epithelial cells and fibroblasts as well as with samples exposed to slightly acidic/basic environments and UV light. For example, the construct is exposed to biological saline solutions buffered to a given pH (ranging between 6.5 to 7.6; Patel et al., 2009 Invest. Ophthalmol. Vis. Sci. 50:2123-2131), and changes in the optical and biomechanical properties of the construct (as well as its ultrastructure) are measured as a function of time. Likewise, the construct is subjected to UV irradiation in a biological safety cabinet, and changes in optical and biomechanical properties are measured.

D. Cell Attachment Behavior

As described in Example I, the construct promotes corneal cell attachment and migration. Stromal fibroblasts are seeded on the surface of the construct and incubated for one hour. The supernatant is removed and the number of cells that have attached is compared to that seeded on the surface to determine the fraction of cells that had attached. Similarly, limbal segments are removed from the cornea and placed on the surface of the construct. Migration of epithelial cells from the limbal segment is monitored for up to seven days. The area covered by epithelial cells is determined using microscopy (brightfield and fluorescent) to observe morphology and viability. Optionally, the surface is modified through the addition of laminin or laminin peptides as described in Example I.

Changes in composition or structure of the construct are not expected to influence attachment of corneal cells. Additional cell attachment studies with endothelial cells are performed to assess the material for use in a fully penetrating keratoprosthesis model.

Example III

Optical and Mechanical Studies

A. Materials and Methods
Collagen-Silica Hybrid Composite Preparation

Tetramethoxysilane (TMOS, 98%, Sigma, St. Louis, Mo.) was used as the silica precursor and was hydrolyzed by sonication with an equal volume of water and 5% v/v 0.01M HCl as a catalyst. This resulted in orthosilic acid, $Si(OH)_4$, or the "sol" (un-solidified silica in the liquid form). The "sol" was mixed with vacuum de-aerated Type I bovine collagen (soluble collagen, Organogenesis; Canton, Mass.) in different concentrations, cast in molds, and allowed to polymerize for 24 hours in a 37° C. incubator. The notation "5/95 TMOS/Collagen" is used to represent the hybrid composite that was produced by mixing 5% v/v silica sol and 95% v/v 4.8 mg/mL collagen. Likewise, hybrid composites representing 10/90 TMOS/Collagen, 20/80 TMOS/Collagen and 25/75 TMOS/Collagen were formed. The concentrations of TMOS and collagen in the hybrid composites are as follows:

5/95 23.5 mg/mL TMOS, 4.56 mg/mL Collagen
10/90 47.0 mg/mL TMOS, 4.32 mg/mL Collagen
20/80 94.0 mg/mL TMOS, 3.84 mg/mL Collagen
25/75 117.5 mg/mL TMOS, 3.6 mg/mL Collagen For transmittance measurements, the collagen-silica mixture was pipetted into a 96-well UV plate (Corning; Corning, N.Y.) at 200 μL per well. For mechanical testing, the hybrid mixture was cast in plastic Petri dishes and further processed as described in section 2.5 Mechanical Testing. To study the microstructure of the hybrid composites, Scanning Electron Microscopy (SEM) and Confocal Raman Microscopy imaging were conducted. SEM was conducted to examine samples' surface topography affected by the variation of samples' composition. Confocal Raman spectroscopy was carried out in order to study the molecular interactions through changes in bond vibration. For SEM, the hybrid mixture was transferred to a 24-well plate (Corning; Corning, N.Y.) at 400 μL per well. For confocal Raman microscopy, 0.5 mm thick silicon adhesive sheets (Invitrogen; Carlsbad, Calif.) were cut with an 8 mm diameter punch and pressed onto microscope slides. The hybrid mixture was cast in the cylindrical molds.

Glucose-mediated Ultraviolet (UV) Crosslinking

Properties of collagen matrix can be controlled through crosslinking. The most commonly used crosslinking agent is glutaraldehyde. However, residual glutaraldehyde has been shown to be cytotoxic (Huang-Lee et al., 1990 J. Biomed. Mater. Res. 24:1185-1201). Alternatives considered include ultraviolet radiation (UV) crosslinking. Glucose is used in combination with UV exposure to reduce the reaction time (Ohan et al., 2002 J. Biomed. Mater. Res. 60:384-391) Glucose (99.5%, Sigma; St. Louis, Mo.) was dissolved in ultra pure water and added to collagen to achieve a final concentration of 0.1% w/v, the physiological concentration in aqueous humor which most commonly used in collagen crosslinking (Marks, 1996 Clinic Chimica Acta 251:19-24; National Aeronautics and Space Administration Technical Support Package. Determining Glucose Levels From NIR Raman Spectra of Eyes. *NASA Tech Brief* 2000 Vol. 24; 14 pages). The collagen concentration was lowered to 4.0 mg/mL due to the addition of glucose solution. The glucose/collagen mixture was placed in the center of a culture hood and exposed to a 39 W UV light for 24 hours to facilitate collagen crosslinking.

Collagen Fibrillogenesis

Collagen fibrillogenesis is an endothermic process. Thermally induced self-assembly of tropocollagen molecule occurs at 37° C. (Heinemann et al., 2009 Acta Biomater. 5:1979-1990). Collagen was placed in a 37° C. incubator for 24 hours to facilitate fibril formation. Collagen fibrils were then used to prepare the hybrid composites as described above.

Optical Measurements

Polymerized hydrogels prepared from tropocollagen, collagen fibril, UV-crosslinked collagen, 10/90 and 25/75 hybrid composites were all transparent. Three replicates of each sample were scanned with spectrophotometer (SpectraMax Plus, Molecular Devices; Sunnyvale, Calif.) for transmittance every 10 nm from 350 nm to 750 nm.

Mechanical Testing

The polymerized hybrid composites were cut into cylindrical samples with a 7 mm diameter punch and dried in a drying chamber at room temperature and 60% RH for 0, 3 hours, or 6 hours before mechanical testing. Uniaxial compression tests were performed at a compression rate of 10 µm/s using a custom designed micro-mechanical tester (IBM Almaden Research Center; San Jose, Calif.) equipped with a 5N load-cell and two parallel metal plates with a diameter of 10 cm. The tests continued until the load-cell's maximum capacity was reached. In the control group (native cornea), 5 mm diameter samples were cut off from the center of human cornea tissue. The cornea tissues were purchased from the Minnesota Lions Eye Banks using a protocol approved by the Institutional Review Board. These samples were deemed unsuitable for transplantation and de-identified. Same experimental procedure was applied on the native corneas as the hybrid composites. Hybrid composites were prepared in cylindrical samples with a larger diameter for easy handling. Native corneas were prepared in cylindrical samples with a smaller diameter since that was the maximum area where the corneas were flat.

Scanning Electron Microscopy (SEM)

The hybrid composites were fixed with 4% formaldehyde in de-ionized water for two hours at room temperature. After three 10-minute washes with ultra-pure water, samples were immersed in 1% osmium tetroxide for one hour at room temperature in the absence of light for secondary fixation, followed by two 10-minute washes with ultra-pure water. The fixed samples were sequentially dehydrated in ultra-pure water/ethanol (50%, 75%, 90% and 100% ethanol) for five minutes each, and in ethanol/hexamethyldisilazane (HMDS) (33%, 67%, and 100% HMDS) for 15 minutes each. The samples were coated with 1 nm platinum using an indirect ion-beam sputter coating system (VCR Group Inc.; San Francisco, Calif.), and examined with a Hitachi S-900 scanning electron microscope (Hitachi; Tokyo, Japan) equipped with a field emission gun at 1-5 kV. As controls, acid soluble collagen was neutralized with 0.1 M NaOH, allowed to polymerize for 24 hours in a 37° C. incubator and prepared for SEM examination as described for the hybrid composites.

Confocal Raman Microscopy

The mechanical properties of the collagenous tissue are affected by the conformation of tropocollagen molecules. Raman microscopy is one of the techniques used to study the chemical and conformational changes in tropocollagen molecule in both aqueous and solid phases. Raman microscopy was conducted using a Witec alpha3000 R confocal Raman microscope (Witec; Ulm, Germany) equipped with UHTS300 spectrometer and DV401 charge-coupled device (CCD) detector. Samples were excited with an Argon ion laser at a wavelength of 514.5 nm and power of 51.6 mW. Data were recorded and analyzed with WitecControl software. To obtain Raman spectra at a single point (300 nm in diameter), the scanning mode of the microscope was set to 'single', and the spectra were collected with an integration time of 10 seconds. As controls, spectra of aqueous collagen and silica were recorded. To obtain 2D Raman images, the scanning mode of the microscope was set to 'depth', and images of the sample's vertical plane parallel to the incident plane of the laser beam were collected with the pixel resolution of 100 points per line and 100 lines per image over an area of 10 µm×10 µm. The integration time used was 0.5 seconds.

Basis analysis was done on the 2D images in order to quantify the homogeneity of the samples. For images rendered from v-$CH_2$ vibration, the bright spots in the 2D images represent collagen rich regions. The intensity of these bright spots was selected as the cutoff to create a Boolean image where the white region represents the presence of collagen and the black region represents its absence. The Boolean image was averaged with the original hybrid spectrum, then underwent basis analysis with the original spectrum to create an image of collagen and an image of the error in this estimation.

B. Results and Discussions

Optical Measurements

Figure 6A:
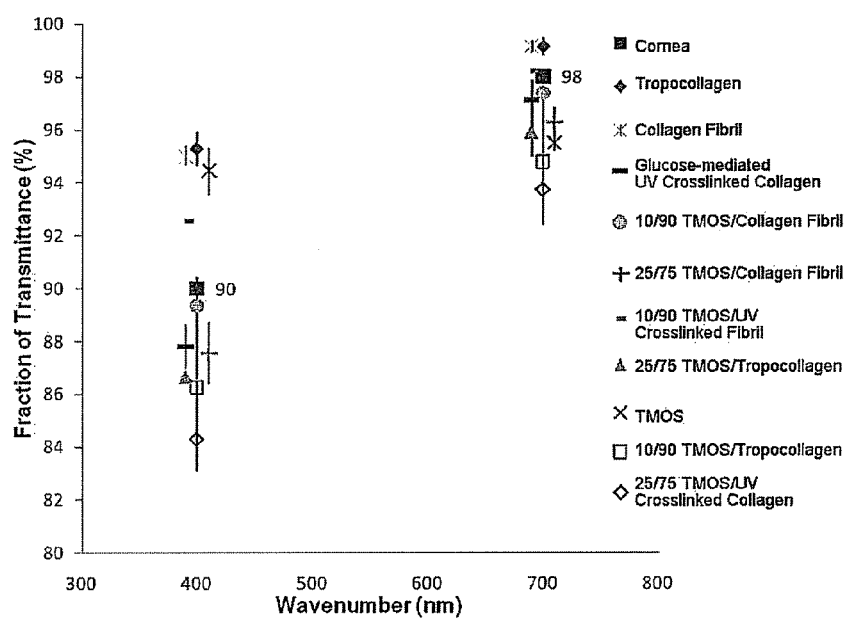
FIG. 6A shows different samples identified by symbols and FIG. 6B shows different samples identified by numbers.
Figure 6B:
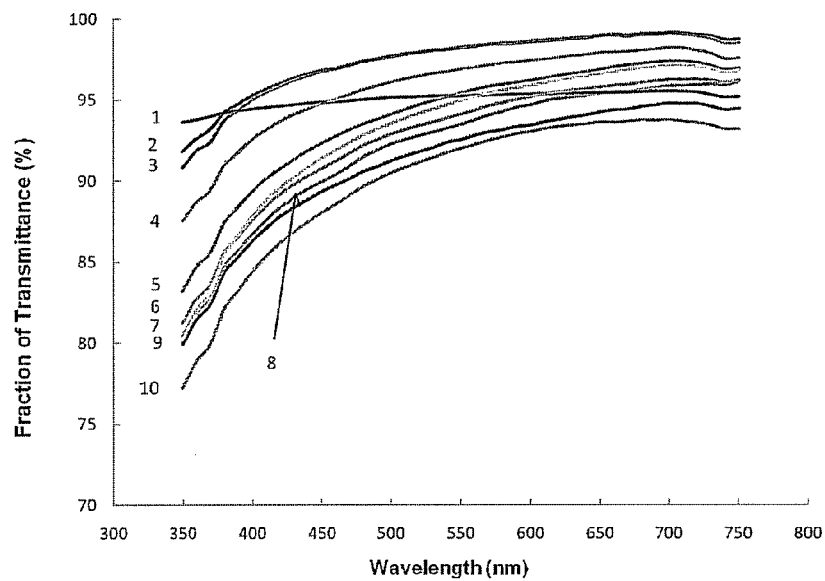

FIG. 6 shows transparency values for silica, collagen and selected hybrid composites over the visible light spectrum. Comparing the fraction of transmittance by composition, pure collagen, regardless of its micro-organization, had the highest transparency of almost 100%, followed by 10/90 hybrid composites, and 25/75 hybrid with lowest transparency. Comparing the fraction of transmittance by the conditioning of collagen, composites made from collagen fibril had the highest transparency, followed by tropocollagen. Light scattering in native cornea is affected by collagen fibril diameter and spacing between collagen fibrils. The decrease in transparency with increasing silica composition suggests a difference in microstructure of the hybrid composites. SEM results suggested that silica encapsulated collagen. It is possible that the silica coating has a different thickness in different hybrid composites due to different TMOS composition in the hybrid. The 25/75 hybrid probably has a thicker coating, therefore it may have a larger fibril diameter and smaller fibril spacing, leading to a lower transmittance measurement. It has been reported that the transparency of collagen hydrogel decreases with crosslinking. The hybrid composites containing crosslinked collagen also had a lower transparency than that of tropocollagen. The results suggested that by proper conditioning and engineering the composition, hybrid composites with desired optical properties can be manufactured.

Figure 7:
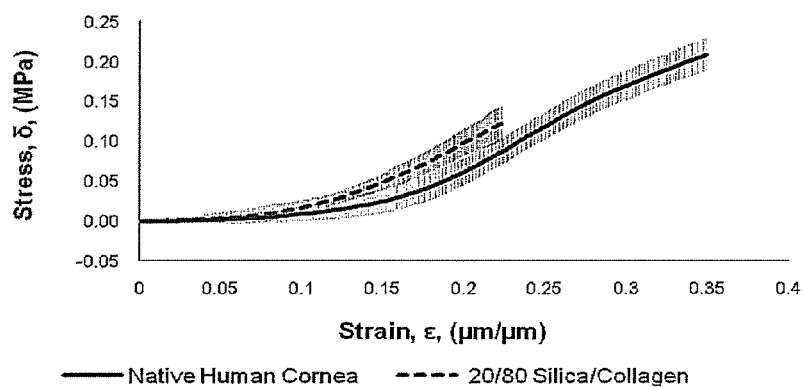
FIG. 7 shows stress-strain plots for native human cornea and 20/80 TMOS/Tropocollagen hybrid composite (dried for six hours at room temperature and 60% RH). Mean±standard deviation is reported. n=5 for native human cornea, and n=3 for the hybrid composite.

Of all composites tested the 20/80 TMOS/Tropocollagen samples showed the most similar stress-strain relation to the native human cornea (FIG. 7). The stress response included a toe region up to 10% strain, followed by a non-linear region, which is typical of biological soft tissues. Since all compression tests were stopped at 5N, the difference in the final stress values was due to the different cross-sectional areas used for the two groups of samples. Therefore, up to 20% strain, within the sample-to-sample variation the compression response of the tissue was very similar to that of the native samples.

Mechanical Testing

Figure 8:
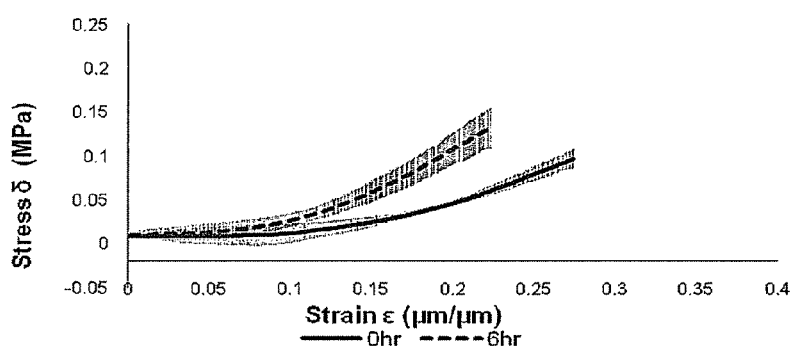
FIG. 8 shows stress-strain plots for 20/80 TMOS/Tropocollagen composite after drying for 0 and 6 hours at room temperature and 60% RH. Mean±standard deviation is reported. n=2 for 0 hours drying, and n=3 for 6 hours drying.

Mechanical properties of the artificial cornea construct depended on collagen and TMOS concentration and post-condensation aging conditions such as temperature, pH and final water content in the composites. Composites with less water content are stiffer. Therefore, composites dried for six hours at 60% relative humidity are stiffer than the fully hydrated composites. Six-hour dried samples can withstand a higher stress than 0 hour dried samples and had a steeper slope in the non-linear region (FIG. 8). In our experiments, the three-hour dried samples had a similar stress response as the six-hour dried samples, starting with a tow region and followed by a non-linear region. Therefore, our experiments showed that after three-hours of drying at room temperature, the composite mechanical properties reached their steady state values.

TABLE 3

Summary of biomechanical (compression) tests conducted on native human cornea and the TMOS/Tropocollagen hybrid composites.

|  |  | Native Human Cornea | 5/95 TMOS/ Tropocollagen | 10/90 TMOS/ Tropocollagen | 20/80 TMOS/ Tropocollagen |
|---|---|---|---|---|---|
| Cornea | $\alpha_1$ | 1.55 ± 0.23 | 0.563 ± 0.192 | 0.911 ± 0.621 | 3.02 ± 1.23 |
| Model[1] | $\beta_1$ | 1.91 ± 0.16 | 3.59 ± 0.76 | 2.39 ± 0.58 | 2.02 ± 0.25 |
| $\delta = \alpha_1 \epsilon^{\beta_1}$ | $R^2$ | 0.9795 | 0.9977 | 0.9954 | 0.9894 |
| Collagen | $\alpha_2$ | 6.05 ± 0.57 | 5.21 ± 0.40 | 6.59 ± 0.66 | 9.70 ± 1.73 |
| Model[2] | $\beta_2$ | 0.0206 ± 0.0028 | 0.00206 ± 0.00235 | 0.00127 ± 0.00025 | 0.00546 ± 0.00200 |
| $\delta = \alpha_2 e^{\beta_2 \epsilon}$ | $R^2$ | 0.9393 | 0.9979 | 0.9933 | 0.9889 |

$\delta$: Engineering stress,
$\epsilon$: Engineering strain.
All hybrid composites were dried for 6 hours at room temperature and 60% RH. n = 5 for native human cornea, and n = 3 for all the other groups.
[1]Fung, Biomechanics: Mechanical Properties of Living Tissues. 2$^{nd}$ Ed, Springer. pg 277.
[2]Fung, Biomechanics: Mechanical Properties of Living Tissues. 2$^{nd}$ Ed, Springer. pg 274.

The experimental data fit very well to both models (0.94<$R^2$<0.99) proposed by Fung while the Cornea Model appeared to be the better of the two (Table 3). $\beta_1$ for 20/80 TMS/Tropocollagen composite is only 6% different from that for native human cornea, while the $\alpha_1$ values are strongly affected by the TMOS concentration. These results showed that the composites can be engineered to resemble the mechanical properties of the native human tissues.

Polymerized collagen hydrogel presented a dense fibrous network with an average fibril diameter of 20±2 nm as measured with ImageJ software. The average diameter of a tropocollagen molecule is 1.5 nm (Kadler et al., 1996 Biochem. J. 316:1-11). The observed fibril is much thicker than a single tropocollagen molecule, suggesting that the tropocollagen molecules do not exist as single molecules in collagen hydrogel. They may self-assemble into fibrils, and this is consistent with fact that collagen triple helices self-assemble into fibril upon an increase in pH (Heinemann et al., 2009 Acta Biomater. 5:1979-1990).

Figure 9:
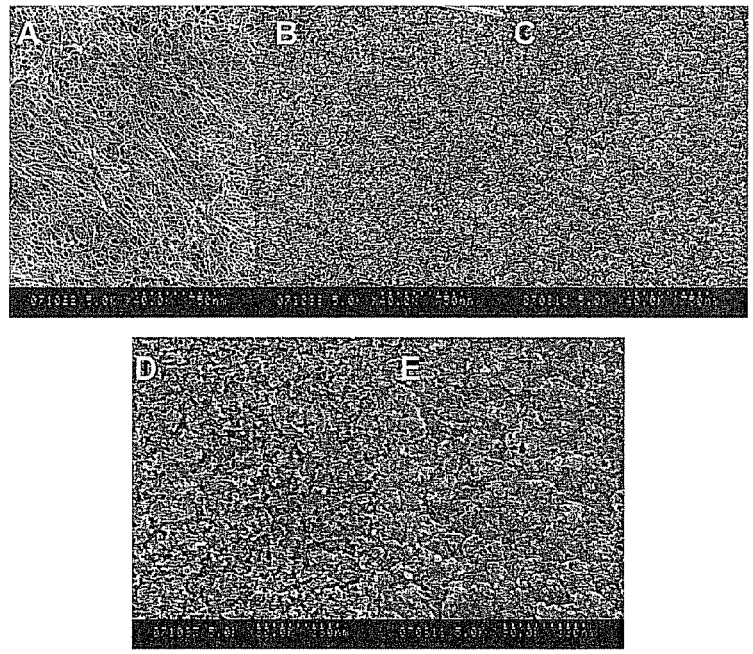
FIG. 9 shows SEM images of polymerized collagen hydrogel and hybrid composites. Collagen hydrogel (A) has a dense fibrous network. 10/90 TMOS/soluble hybrid composite (B) has a smaller grain size than 25/75 TMOS/Tropocollagen hybrid composite (C). At a higher magnification, 10/90 TMOS/Collagen hybrid composite (D) is more porous than 25/75 TMOS/Collagen hybrid composite (E).
Figure 10:
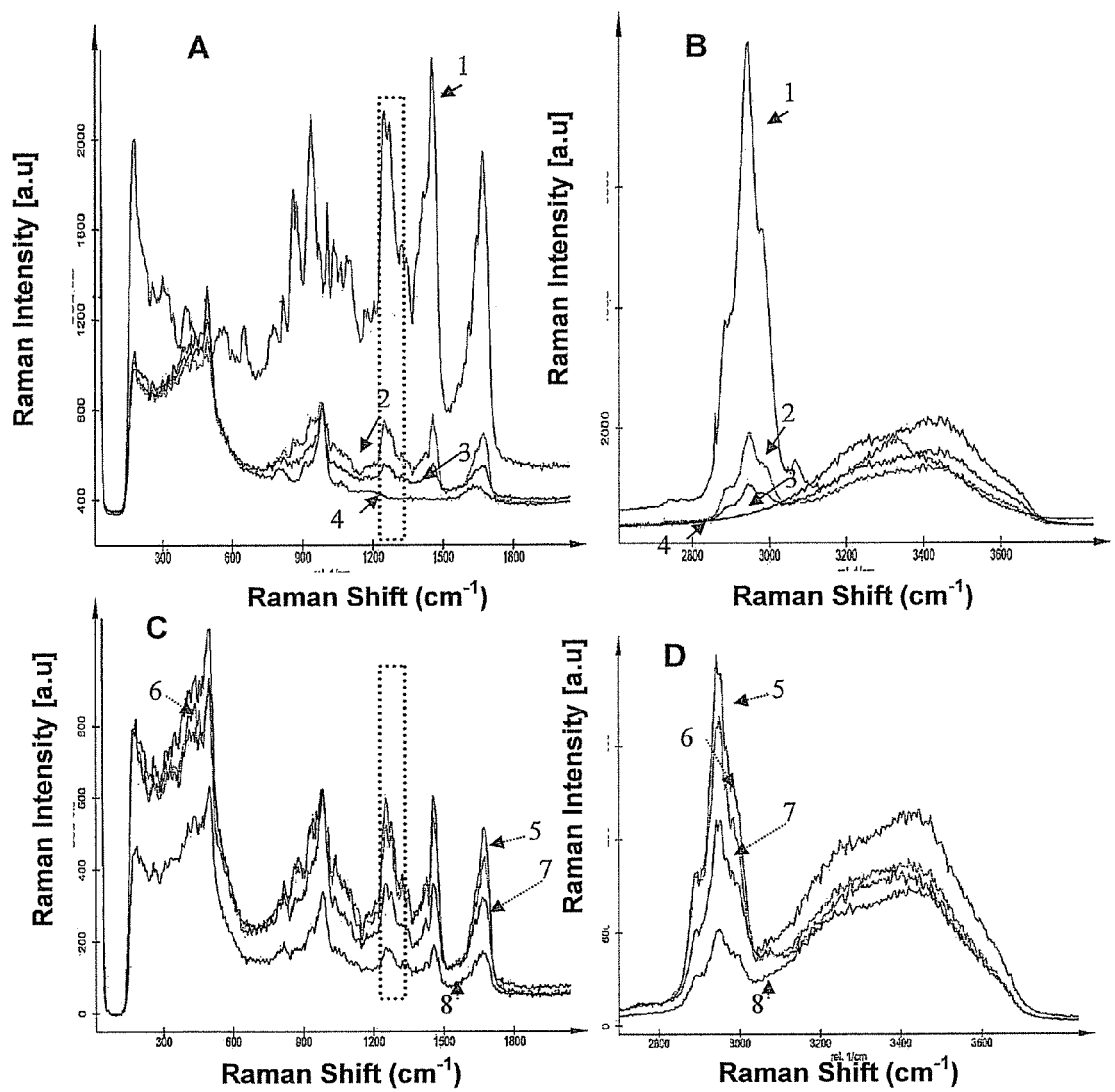
FIG. 10 shows Raman spectra of collagen, silica and hybrid composites: 1, Tropocollagen; 2, 10/90 TMOS/Tropocollagen; 3. 25/75 TMOS/Tropocollagen; 4, TMOS; 5, 10/90 TMOS/Collagen Fibril; 6, 25/75 TMOS/Collagen Fibril; 7, 10/90 TMOS/UV-crosslinked collagen; 8, 25/75 TMOS/UV-crosslinked collagen. Amide peaks and Si—O—Si peak are shown in A and C. C—H peak and O—H peak are shown in B and D. Amide III peaks were highlighted with dotted lines in both figures A and C. This is the region used where curve-fitting and area ratio calculation were done.

The polymerized hybrid composites had granular structures uniformly distributed across the surface of the samples. 10/90 TMOS/Tropocollagen composite had an average grain diameter of 0.090 nm, which is smaller than that of the 25/75 Silica/Tropocollagen hybrid (0.135 nm). The 25/75 TMOS/ Tropocollagen hybrid composites have more circular and uniform grains than the 10/90 hybrid. At a higher magnification (FIG. 9), both composites appeared to be nanoporous with the 10/90 TMOS/Tropocollagen composite being more porous. Many research groups suggested both collagen molecules and collagen fibrils can be the organic template for silicification in the sol-gel process (Heinemann et al., 2009 Acta Biomater. 5:1979-1990; Ye et al., 2008 Appl. Surface Sci. 254:5975-5980). Comparing the SEM images of the hybrid with that of the collagen, it is possible that the collagen network provides the site for silica condensation during the gel formation, at least on the outmost layer of the network. The topography and porosity of the hybrid composites are affected by the silica-collagen composition, suggesting that the composites can be engineered to achieve the desired topography and porosity for cell culture in the future.

The broad band centered between 3320 cm$^{-1}$ and 3440 cm$^{-1}$ is assigned to the v-OH vibration in collagen and absorbed water. The C—H vibration at 2944 cm$^{-1}$ is the characteristic peak for organic matter, which is collagen in this case. When taking the spectra, the alignment of the samples and associated adjustments were conducted visually by monitoring these two signals since they are stronger. The assignment of major Raman peaks was summarized in Table 4.

TABLE 4

Summary of the major Raman peaks

| Wavenumber (cm$^{-1}$) | Assignment |
|---|---|
| 2944 | C—H[a] |
| 1671, 1646 | Amide I[b] |
| 1454 | Amide II[b] |
| 1270 | Amide III (polar region)[b] |
| 1249 | Amide III (non-polar region)[b] |
| 1008 | Phenylalanine (side chain)[b] |
| 988 | Si—OH[c] |
| 862 | Proline (side chain)[c] |
| 876 | Hydroxyproline (side chain)[b] |
| 492 | Si—O—Si[c] |

[a]Dehring et al., 2006 Appl. Spectroscopy 60: 366-372
[b]Frushour and Koeing, 1975 Biopolymers 14: 379-391
[c]Gailliez-Degremont et al., 1998 J. Appl. Polymer Sci. 65: 871-882

TABLE 5

Summary of area ratio (1249 cm$^{-1}$ band:1270 cm$^{-1}$ band) in amide III region.

| Hybrid Composites | Area Ratio | $r^2$ |
|---|---|---|
| Tropocollagen | 0.5021 | 0.9953 |
| 10/90 TMOS/Tropocollagen | 0.6304 | 0.9860 |
| 25/75 TMOS/Tropocollagen | 3.428 | 0.9823 |
| 10/90 TMOS/Collagen Fibril | 0.6415 | 0.9680 |
| 25/75 TMOS/Collagen Fibril | 0.8339 | 0.9622 |
| 10/90 TMOS/UV-crosslinked Collagen | 0.8144 | 0.9414 |
| 25/75 TMOS/UV-crosslinked Collagen | 0.7802 | 0.9486 |

There are two peaks in amide III region: 1270 cm$^{-1}$ and 1249 cm$^{-1}$. It can be assigned to the polar and non-polar regions of the collagen polypeptide chains, according to Frushour (Frushour and Koeing, 1975 Biopolymers 14:379-391), or α-helices and random coil content in collagen, according to Dehring (Dehring et al., 2006 Appl. Spectroscopy 60:366-372). Regardless of the pre-conditioning of collagen (whether it is tropocollagen, collagen fibril or UV-crosslinked collagen), the 1270 cm$^{-1}$ signal appeared weaker in the 10/90 hybrid composites, and became a shoulder in the 25/75 hybrid composite. This suggested that the polar region of collagen was involved in the interaction with silica. N—H bond vibration is the primary contributor to the peaks in amide III regions (Frushour and Koeing, 1975 Biopolymers 14:379-391). N—H bond is polar and it is in favor of hydrogen bonding or electrostatic interaction with the hydroxyl group found on the surface of silica hydrogel (Ye et al., 2008 Appl. Surface Sci. 254:5975-5980).

To quantify the change in the polar region of collagen polypeptide chain, curve fitting was performed on peaks in amide III region using PeakFit 4 and area ratio of 1249 cm$^{-1}$ band and 1274 cm$^{-1}$ band was calculated. An increase in area ratio indicates a decrease in the relative content of the polar region, suggesting the polar region of collagen is involved in the interaction with silica. All hybrid composites have higher area ratios than the tropocollagen molecule. This agrees with the statement that hydrogen bonding existed between collagen and silica. The 25/75 TMOS/Tropocollagen hybrid has the highest area ratio, implying an extensive hydrogen bonding existed in the composite. In terms of the secondary structure of collagen polypeptide chain, the increase in area ratio indicates an increase in disorder in the hybrid composites, suggesting the interaction with silica may loosen or pull apart the helical structure in collagen.

Figure 11:
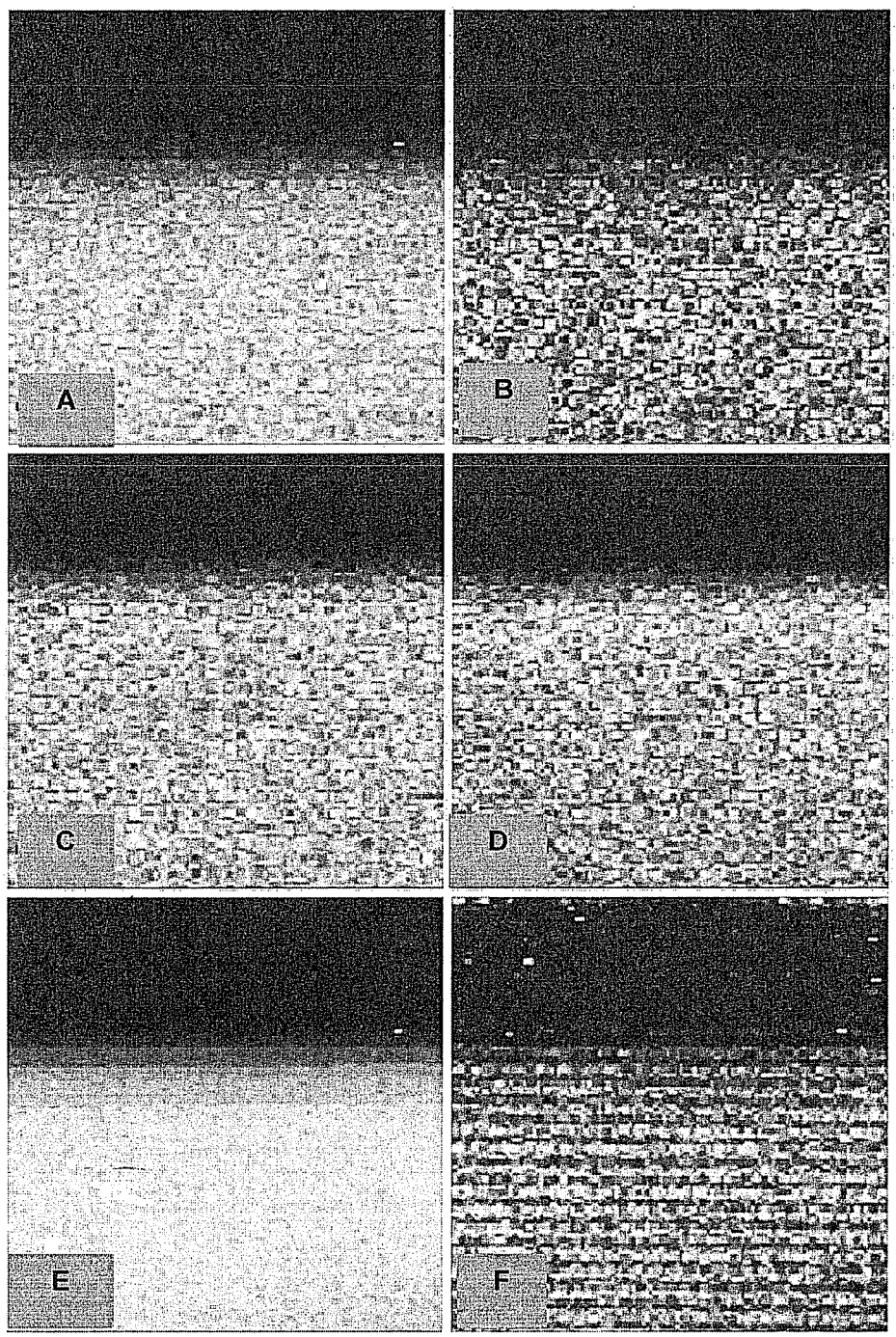
FIG. 11 shows 2D Raman images of hybrid composites made from tropocollagen. 10/90 hybrid rendered from v-CH$_2$ vibration: A, the raw image; E analyzed image; F basis analysis error. 10/90 hybrid image rendered from v-SiO vibration: B, the raw image; G analyzed image; H basis analysis error. 25/75 hybrid composite image rendered from v-CH$_2$ vibration: C, the raw image; I analyzed image; J basis analysis error. Images of 25/75 hybrid rendered from v-SiO vibration: D, the raw image; K analyzed image; L basis analysis error. The bright spots represent errors in the estimation. All images were taken with the same scale bar of 2 μm.
Figure 11:
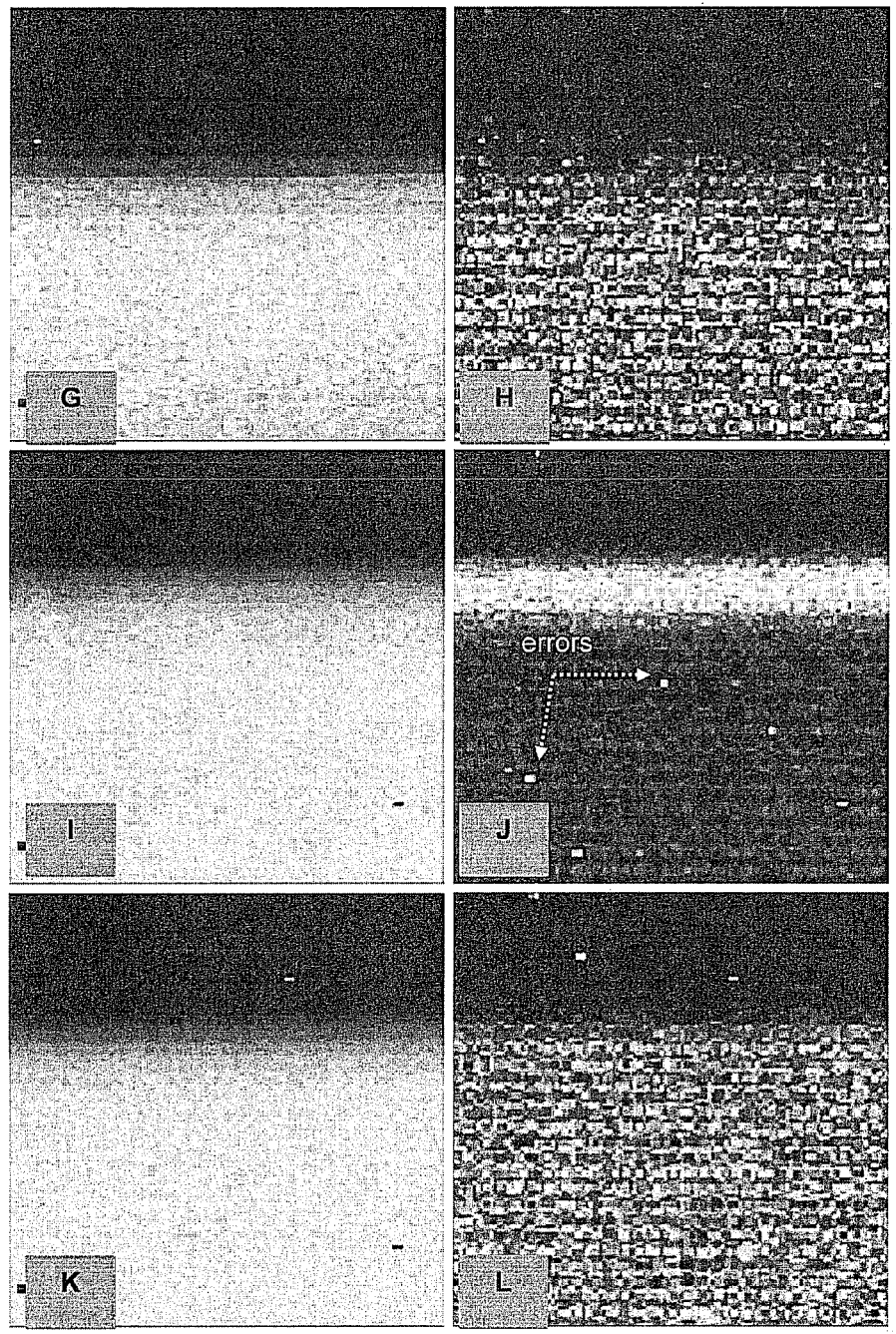
Figure 12:
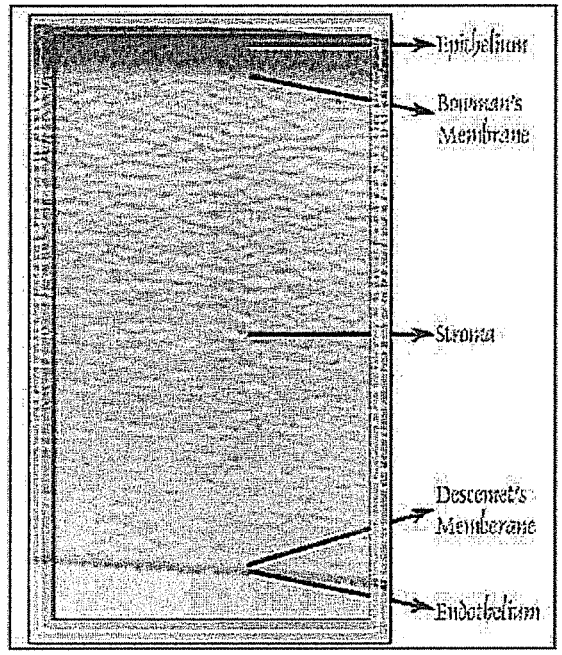
FIG. 12 shows the layers of the cornea.
Figure 13:
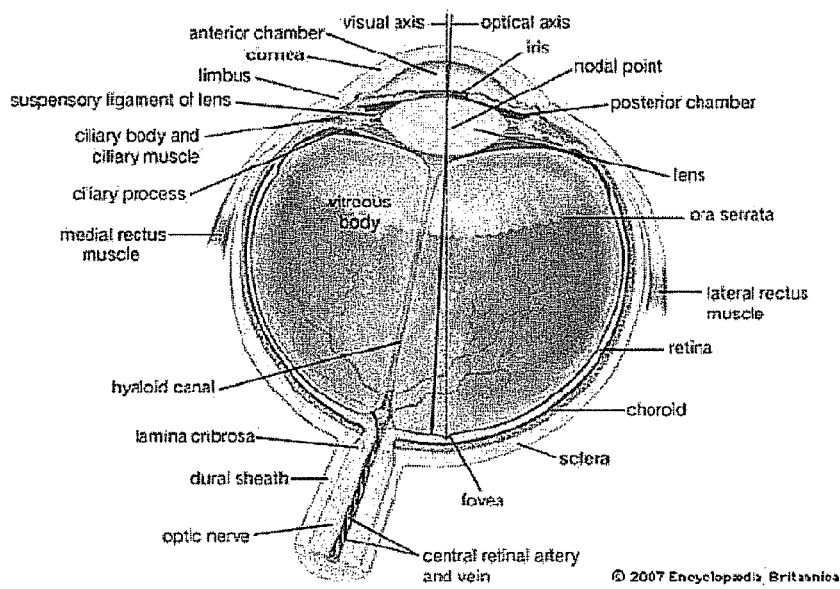
FIG. 13 shows the anatomy of the eye.

The 2D Raman images were taken at a vertical plane parallel to the incident laser beam starting from the surface of the sample. In the analyzed images, a uniform color distribution was seen in both 10/90 and 25/75 hybrid composites, suggesting a uniform distribution of collagen and silica cross the vertical plane of the hybrid composites. The bright spots in the basis analysis error images were the deviations in our estimation. A few error spots appeared only in FIG. 11J, the 25/75 hybrid rendered from v-CH$_2$ vibration. In general, our analysis was accurate. The error in the collagen image for the 25/75 hybrid may not be due to the inaccuracy of the estimation. The other possible reason could be the image's sensitivity to the selected cutoff value. The smaller collagen composition in the 25/75 hybrid lead to a less intense image rendered from v-CH$_2$ vibration, and less data points selected. A small change in the cutoff intensity would result in a large change in the number of data points selected for rendering the image. Therefore, the 25/75 hybrid image was more sensitive to the intensity cutoff value, resulting in a higher probably of making errors in the estimation.

Example IV

Biocompatibility Studies

The cornea creates the barrier between the inner eye and the outside world, and is responsible for a majority of the light refraction into the eye. It is made up of five separate layers, with the stroma accounting for 90% of the thickness. The cornea is home to three separate cell types. The epithelium is located on the most anterior portion of the eye and is responsible for keeping water and other debris out of the stroma. The stroma is made of collagen and is where the fibroblast cells survive and organize the layers of collagen. The most posterior cornea is the location of the endothelial cells, which act as a pump between the stroma and the aqueous.

A hybrid gel of TMOS (silica) and collagen was tested for its ability to support attachment of two cells found in the cornea: stromal fibroblast and corneal epithelial cells. The harvested fibroblast cells were allowed to attach to the hybrid gel, pure collagen gel, and pure TMOS gel for one and 24 hours, and their attachment was studied both qualitatively and quantitatively. The study was repeated with adsorbed laminin on the hybrid and TMOS gels, and again with the YIGSR (SEQ ID NO:1) domain adsorbed to the hybrid and TMOS gels.

Cells attached relatively well to all of the uncoated materials. The lowest percentage of cells attached after one hour was 66% to the TMOS gel. The uncoated hybrid gel was slightly better having 75% of the cells attach after one hour. The adsorption of laminin greatly increased the amount of cells attached, making all of the gels relatively equal having approximately 95% of the cells attach within one hour.

Materials and Methods

Cell Isolations

Human corneas were obtained from the Lions Eye Bank (Minneapolis, Minn.) with approval from the local Institutional Review Board. Isolation of corneal epithelial cells involved tissue culture of limbal segments excised from corneas. The limbal segments were cut into approximately 5 mm×5 mm segments and were placed at four segments per well in a 6-well culture plate and incubated overnight.

Isolation of corneal epithelial cells may also involve cutting the cornea into quarters and incubating in dispase at 4° C. refrigerator overnight. Corneal segment incubated overnight were vortexed to break up any large epithelial cell clumps and seeded into 6-well culture plates with the appropriate media.

Isolation of stromal fibroblasts was performed by placing corneal segments in a collagenase solution and incubating. After incubation, the corneal pieces and cells were strained through a cell strainer, and the pieces were rinsed with stromal fibroblast media. After centrifugation, the supernatant was poured off and the fibroblast cells were re-suspended and plated into two wells of a 6-well culture plate.

Cell Attachment Study

Corneal Stromal Fibroblasts

Gels were normally prepared in the way described previously. Corneal stromal fibroblast cells were counted, resuspended in fibroblast media and seeded on the surface of a hybrid matrix. After one hour, excess media was removed and unattached cells were counted. Cells attached to the surface were imaged using AO/PI fluorescent. Imaging of cells attached to the surface was repeated after 24 hours of incubation. The process was repeated two more times with a different protein adsorbed to the gel in each of the new trials. The proteins used were laminin and the YIGSR (SEQ ID NO:1) domain.

Figure 14:
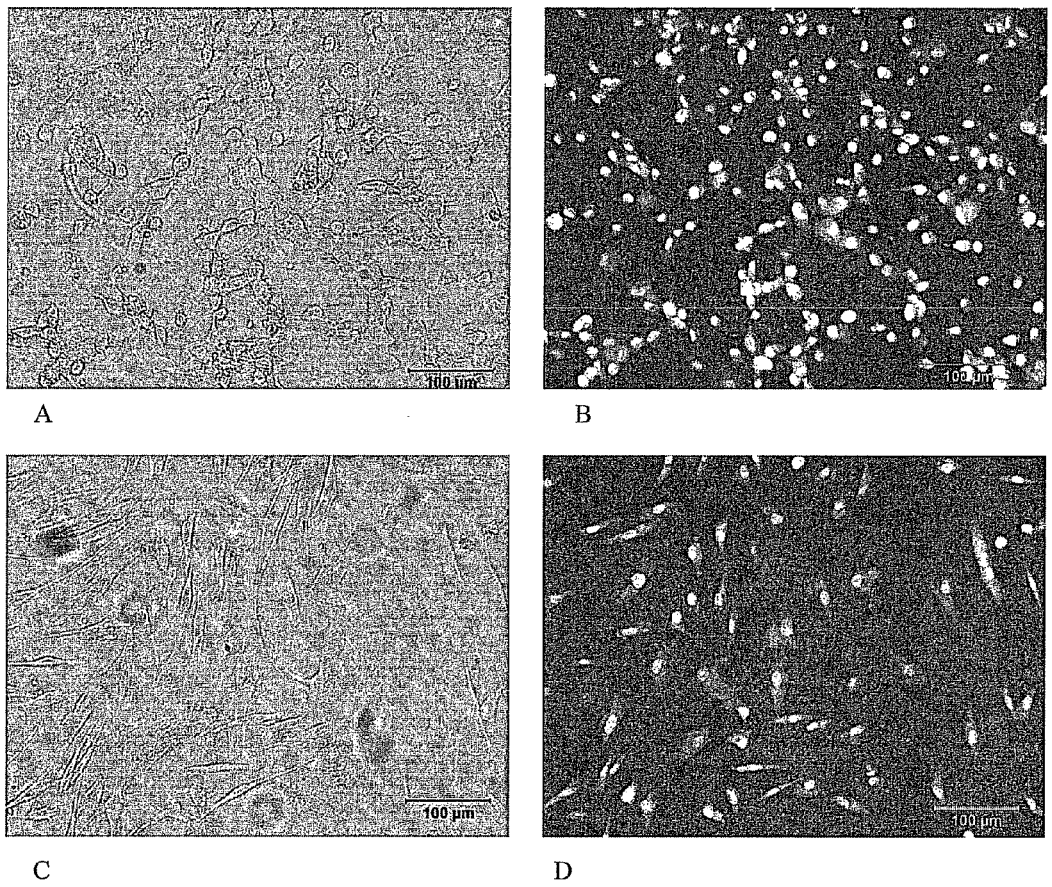
FIG. 14 shows control—collagen gel with no coating at one hour (A and B) and 24 hours (C and D). Panels A and C show bright field images and Panels B and D show fluorescent images.

The collagen gels were used as a control for all of the trials. Shown in FIG. 14 are the bright field and fluorescent pictures of corneal stromal fibroblasts, both one hour and 24 hours after they were seeded on collagen gels. Pictures A and B show the cells one hour after seeding, and were taken from the YIGSR (SEQ ID NO:1) domain study. It can be seen that the cells readily attached to the collagen within one hour, and that the cells were beginning to attach and form the elongated shape that they normally exhibit in culture. The attachment and spreading of the cells was complete by 24 hours.

Figure 15:
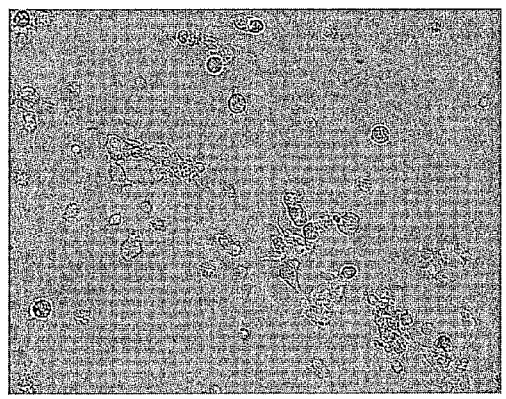
FIG. 15 shows hybrid gel with no coating at one hour (A and B) and 24 hours (C and D). Panels A and C show bright field images and Panels B and D show fluorescent images.
Figure 15:
Figure 15:
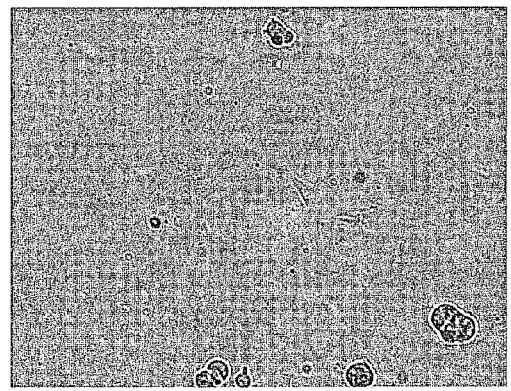
Figure 15:
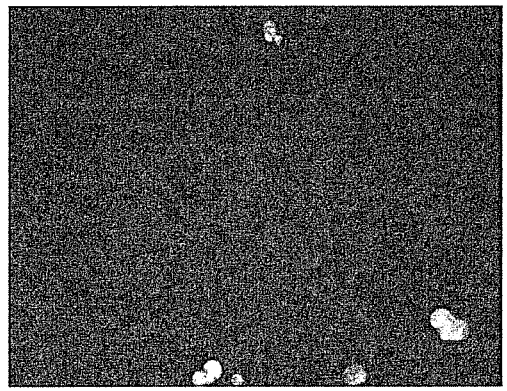

FIG. 15 shows the attachment of the fibroblast cells to the hybrid gel with no surface modification. Pictures C and D show the attachment of the cells after they have been on the gel for 24 hours.

Figure 16:
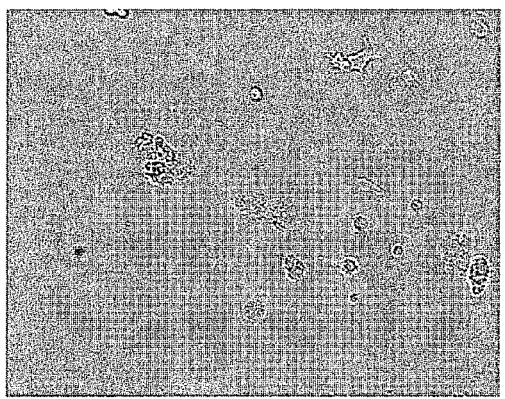
FIG. 16 shows TMOS gel with no coating at one hour (A and B) and 24 hours (C and D). Panels A and C show bright field images and Panels B and D show fluorescent images.
Figure 16:
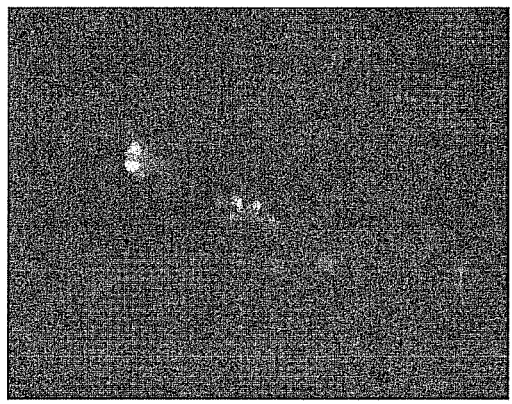
Figure 16:
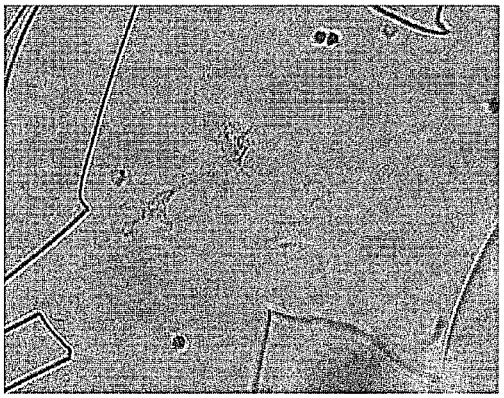
Figure 16:
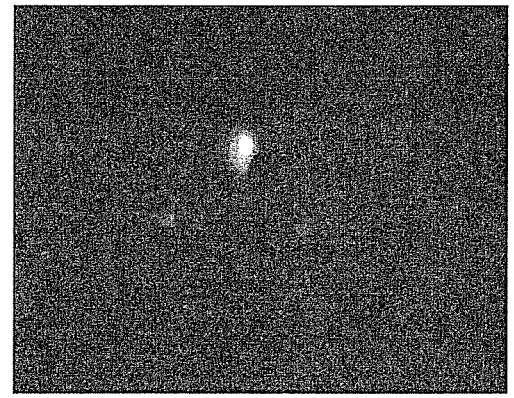

The uncoated TMOS pictures at 1 and 24 hours are shown in FIG. 16. There are a few fibroblast cells that appear to be in the process of attaching after one hour on the gel. After 24 hours of incubation time, the bright field image (A) shows multiple cells that have successfully attached to the gel.

Figure 17:
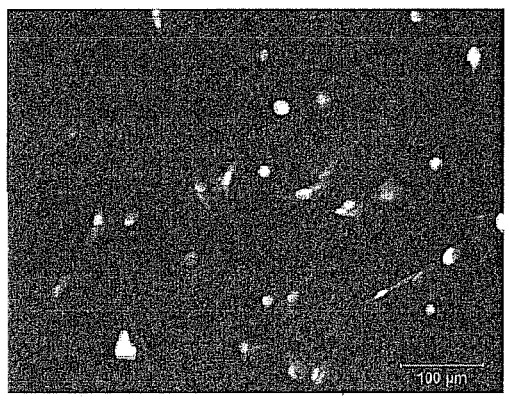
FIG. 17 shows TMOS gel coated with laminin at one hour (A and B) and 24 hours (C and D). Two fluorescent images are shown for the one hour pictures. Panel C shows a bright field image and Panels A, B, and D show fluorescent images.
Figure 17:
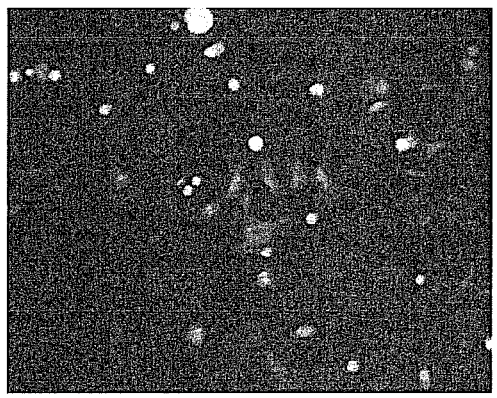
Figure 17:
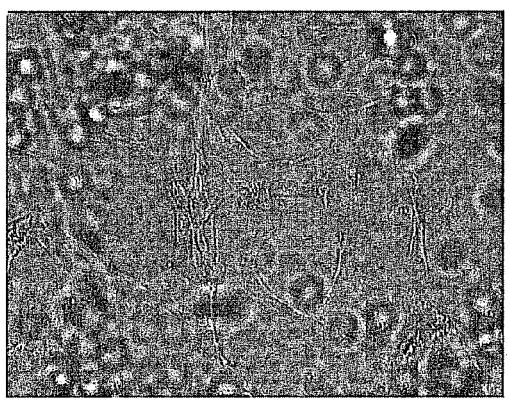
Figure 17:
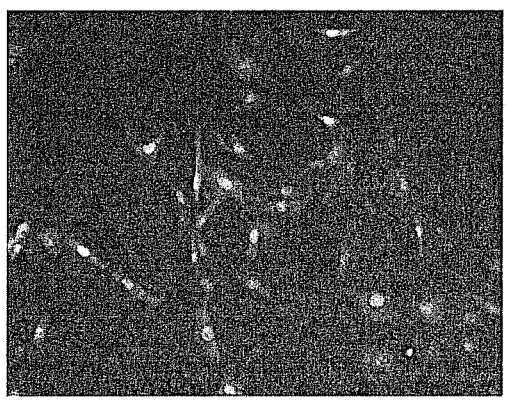

The laminin coated TMOS gels are shown in FIG. 17. A significant number of cells attached to the surface after one hour of incubation. Two fluorescent images, are shown in A and B. By the time the cells had been on the gel for 24 hours, all of the cells showed good attachment, as shown in images C and D.

Figure 18:
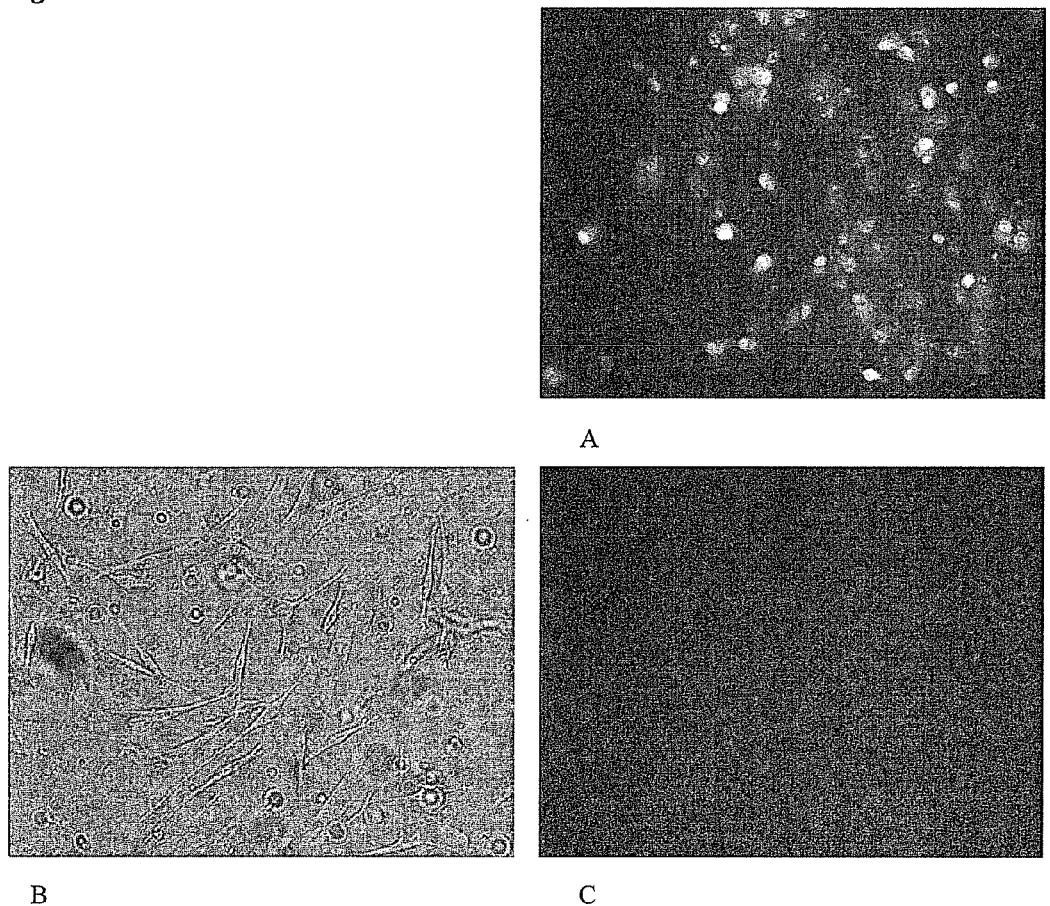
FIG. 18 shows hybrid gel coated with laminin at one hour (A) and 24 hours (B and C). No brightfield image was taken after cells had been seeded for one hour. Panel B shows a bright field image and Panels A and C show fluorescent images.

The images from the laminin coated hybrid gel are shown in FIG. 18. After one hour of incubation, Image A shows many cells attached to the gel. Images B and C show that after 24 hours on the gel, all of the cells were attached and exhibited their normal morphology.

Figure 19:
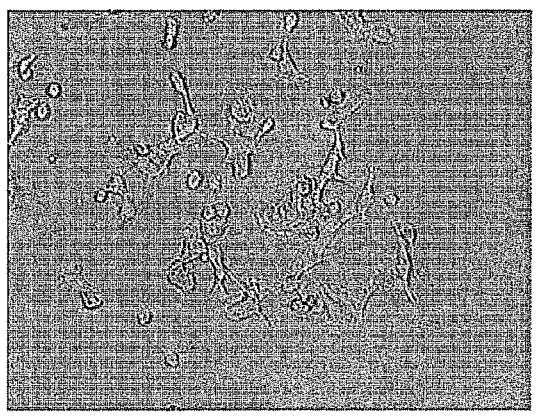
FIG. 19 shows TMOS gel coated with the YIGSR domain at one hour (A and B) and 24 hours (C and D). Panels A and C show bright field images and Panels B and D show fluorescent images.
Figure 19:
Figure 19:
Figure 19:
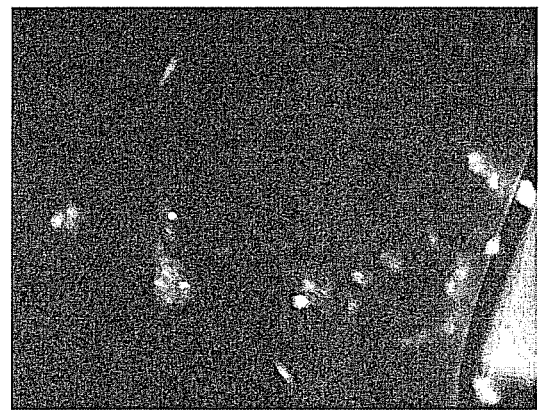

The fibroblast attachment to the YIGSR (SEQ ID NO:1) coated TMOS gels are shown in FIG. 19. The cells started to attach after one hour of incubation. After 24-hours of incubation, cells appear to attached well but have not returned to their normal morphology completely after 24 hours time.

Figure 20:
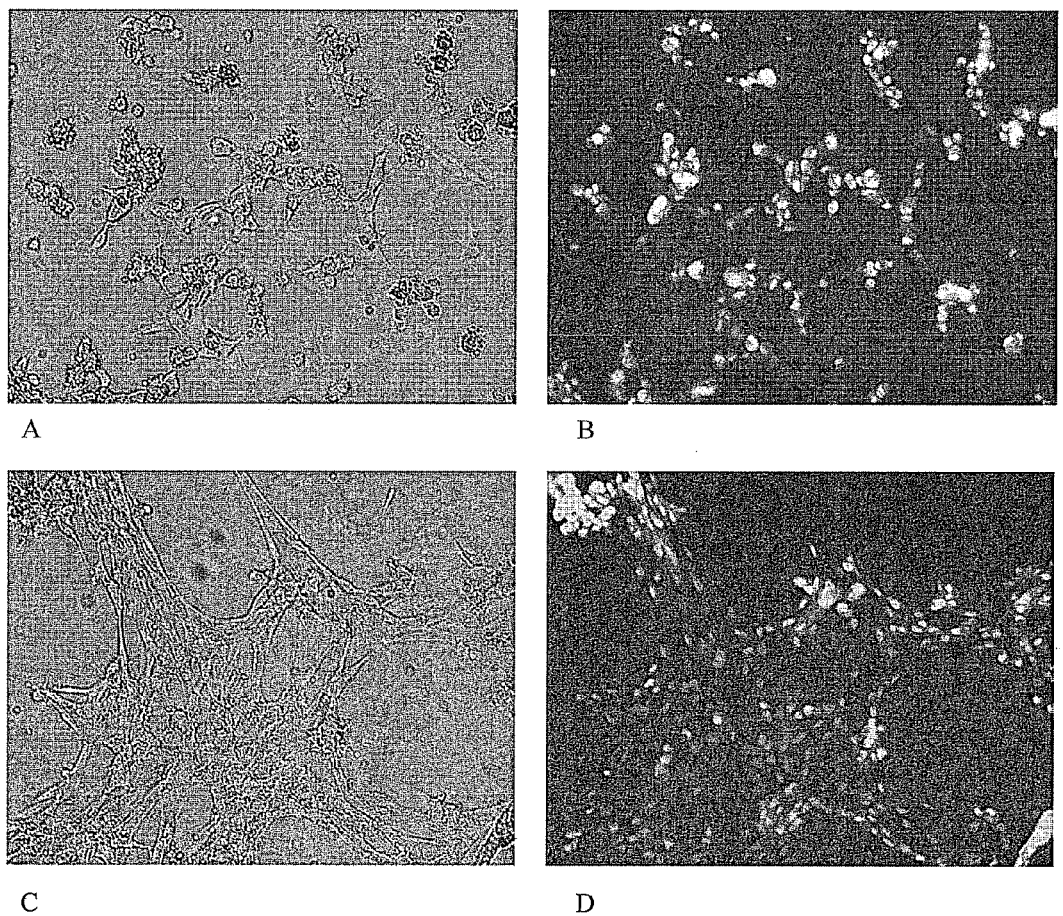
FIG. 20 shows hybrid gel coated with the YIGSR domain at one hour (A and B) and 24 hours (C and D). Panels A and C show bright field images and Panels B and D show fluorescent images.
Figure 21:
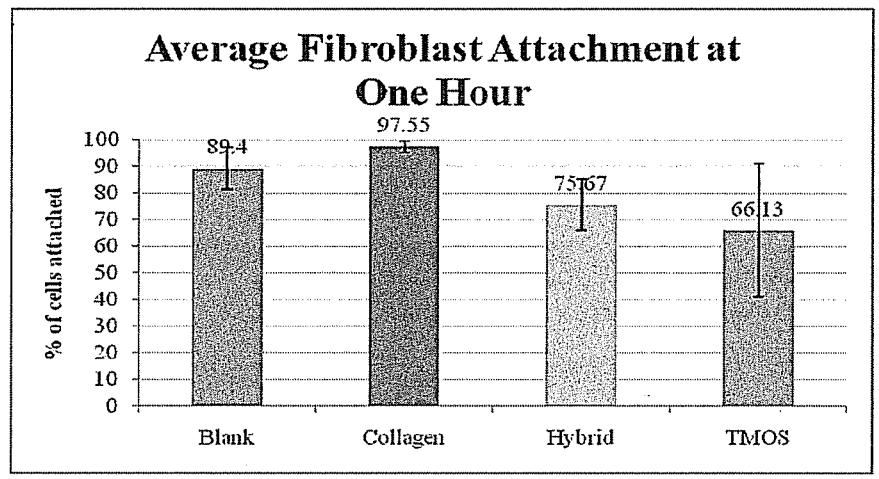
FIG. 21 shows the average attachment of fibroblast cells to with n=3 uncoated gels.

The fibroblast attachment to the YIGSR (SEQ ID NO:1) coated hybrid gels is shown in FIG. 20. Many cells have attached and have begun elongating and flattening after one hour on the gel. After twenty-four hours, all of the cells have attached well to the material and are bound together into a large cluster.

Figure 22:
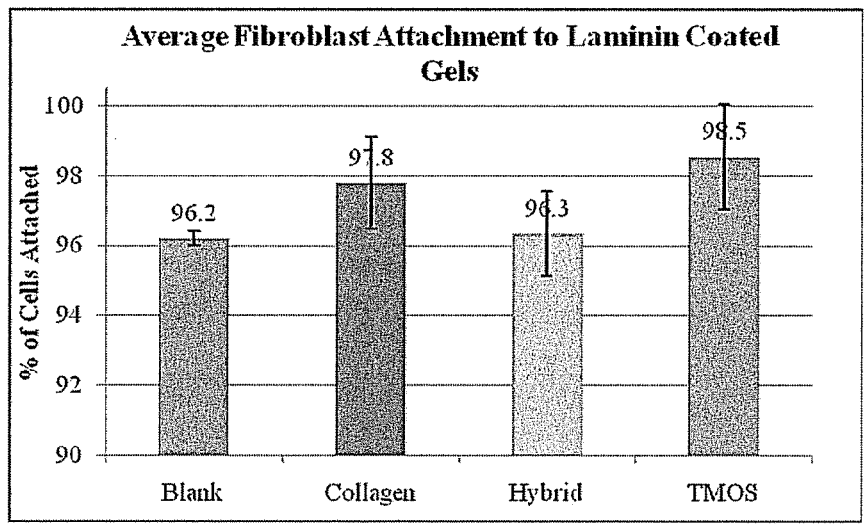
FIG. 22 shows the average fibroblast attachment to laminin coated gels with n=3 gels of each type.

The attachment of corneal stromal fibroblasts for the different substrates is shown in FIG. 22. These values were obtained from an average count from three of the same type of gels seeded at the same density. The average for the wells without gel was almost 90% with a standard deviation of 8. The average for the collagen gel was higher than that with 98% of the cells attaching to the gel, with a standard deviation of 2. The hybrid saw three fourths of the cells attach to the gel with a standard deviation of 9.5. The TMOS had two thirds of the seeded cells attach with a standard deviation of 25.

All of the gels coated with laminin yielded percent attached values higher than 95%, as shown in FIG. 23. The lowest value was the blank (uncoated) well at 96.2% with a standard deviation of 0.2. The next lowest was the hybrid gel having 96.3% of the seeded cells attach, with a standard deviation of 1.3. The second best attachment was the collagen gel at 97.8% of the cells attaching, with a standard deviation of 1.2. The best attachment occurred on the TMOS gel with a standard deviation of 1.5.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

SEQUENCE FREE TEXT LISTING

1: YISGR laminin subunit polypeptide
2: IKVAVYIGSR laminin subunit polypeptide
3: (Pro-Hyp-Gly)$_{10}$ collagen mimetic peptide
4: (PHypG)$_{10}$-SGSGSG-YIGSR collagen mimetic peptide conjugate
5: (PHypG)$_{10}$-IKVAVYIGSR collagen mimetic peptide conjugate
6: SGSGSG flexible peptide linker

What is claimed is:

1. A corneal implant comprising a structure formed from an optically clear, biocompatible composite comprising a fibrillar component and a silica component coating at least a portion of the fibrillar component.

2. The corneal implant of claim 1 wherein the fibrillar component is collagen.

3. The corneal implant of claim 2 wherein the fibrillar component is soluble collagen.

4. The corneal implant of claim 1 further comprising a cytophilic biomolecule.

5. The corneal implant of claim 4 wherein the cytophilic biomolecule comprises laminin or a polypeptide comprising a subunit of laminin, wherein said subunit contains at least 5 amino acids.

6. The corneal implant of claim 5 wherein the laminin subunit comprises the amino acid sequence YIGSR (SEQ ID NO:1).

7. The corneal implant of claim 1 further comprising an osmolyte.

8. The corneal implant of claim 1 comprising a silica component/fibrillar component ratio of from 40:1 to 1:40.

9. A contact lens comprising a structure formed from an optically clear, biocompatible composite comprising a fibrillar component and a silica component coating at least a portion of the fibrillar component.

10. The contact lens of claim 9 wherein the fibrillar component is collagen.

11. The contact lens of claim 10 wherein the fibrillar component is soluble collagen.

12. The contact lens of claim 9 further comprising an osmolyte.

13. The contact lens of claim 9 further comprising a therapeutic agent.

14. The contact lens of claim 9 fabricated to protect the eye or promote healing of eye tissue.

15. The contact lens of claim 9 comprising a silica component/fibrillar component ratio of from 40:1 to 1:40.

* * * * *

```
                      SEQUENCE LISTING

<160> NUMBER OF SEQ ID NOS: 6

<210> SEQ ID NO 1
<211> LENGTH: 5
<212> TYPE: PRT
<213> ORGANISM: artificial
<220> FEATURE:
<223> OTHER INFORMATION: laminin subunit polypeptide

<400> SEQUENCE: 1

Tyr Ile Ser Gly Arg
1               5

<210> SEQ ID NO 2
<211> LENGTH: 10
<212> TYPE: PRT
<213> ORGANISM: artificial
<220> FEATURE:
<223> OTHER INFORMATION: laminin subunit polypeptide

<400> SEQUENCE: 2

Ile Lys Val Ala Val Tyr Ile Gly Ser Arg
1               5                   10

<210> SEQ ID NO 3
<211> LENGTH: 30
<212> TYPE: PRT
<213> ORGANISM: artificial
<220> FEATURE:
<223> OTHER INFORMATION: collagen mimetic peptide
<220> FEATURE:
<221> NAME/KEY: MISC_FEATURE
<222> LOCATION: (2)..(2)
<223> OTHER INFORMATION: proline at position 2 is a hydroxyproline
```

```
<220> FEATURE:
<221> NAME/KEY: MISC_FEATURE
<222> LOCATION: (5)..(5)
<223> OTHER INFORMATION: proline at position 5 is a hydroxyproline
<220> FEATURE:
<221> NAME/KEY: MISC_FEATURE
<222> LOCATION: (8)..(8)
<223> OTHER INFORMATION: proline at position 8 is a hydroxyproline
<220> FEATURE:
<221> NAME/KEY: MISC_FEATURE
<222> LOCATION: (11)..(11)
<223> OTHER INFORMATION: proline at position 11 is a hydroxyproline
<220> FEATURE:
<221> NAME/KEY: MISC_FEATURE
<222> LOCATION: (14)..(14)
<223> OTHER INFORMATION: proline at position 14 is a hydroxyproline
<220> FEATURE:
<221> NAME/KEY: MISC_FEATURE
<222> LOCATION: (17)..(17)
<223> OTHER INFORMATION: proline at position 17 is a hydroxyproline
<220> FEATURE:
<221> NAME/KEY: MISC_FEATURE
<222> LOCATION: (20)..(20)
<223> OTHER INFORMATION: proline at position 20 is a hydroxyproline
<220> FEATURE:
<221> NAME/KEY: MISC_FEATURE
<222> LOCATION: (23)..(23)
<223> OTHER INFORMATION: proline at position 23 is a hydroxyproline
<220> FEATURE:
<221> NAME/KEY: MISC_FEATURE
<222> LOCATION: (26)..(26)
<223> OTHER INFORMATION: proline at position 26 is a hydroxyproline
<220> FEATURE:
<221> NAME/KEY: MISC_FEATURE
<222> LOCATION: (29)..(29)
<223> OTHER INFORMATION: proline at position 29 is a hydroxyproline

<400> SEQUENCE: 3

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 4
<211> LENGTH: 41
<212> TYPE: PRT
<213> ORGANISM: artificial
<220> FEATURE:
<223> OTHER INFORMATION: collagen mimetic peptide conjugate
<220> FEATURE:
<221> NAME/KEY: MISC_FEATURE
<222> LOCATION: (2)..(2)
<223> OTHER INFORMATION: proline at position 2 is a hydroxyproline
<220> FEATURE:
<221> NAME/KEY: MISC_FEATURE
<222> LOCATION: (5)..(5)
<223> OTHER INFORMATION: proline at position 5 is a hydroxyproline
<220> FEATURE:
<221> NAME/KEY: MISC_FEATURE
<222> LOCATION: (8)..(8)
<223> OTHER INFORMATION: proline at position 8 is a hydroxyproline
<220> FEATURE:
<221> NAME/KEY: MISC_FEATURE
<222> LOCATION: (11)..(11)
<223> OTHER INFORMATION: proline at position 11 is a hydroxyproline
<220> FEATURE:
<221> NAME/KEY: MISC_FEATURE
<222> LOCATION: (14)..(14)
<223> OTHER INFORMATION: proline at position 14 is a hydroxyproline
<220> FEATURE:
<221> NAME/KEY: MISC_FEATURE
<222> LOCATION: (17)..(17)
<223> OTHER INFORMATION: proline at position 17 is a hydroxyproline
<220> FEATURE:
<221> NAME/KEY: MISC_FEATURE
<222> LOCATION: (20)..(20)
```

```
<223> OTHER INFORMATION: proline at position 20 is a hydroxyproline
<220> FEATURE:
<221> NAME/KEY: MISC_FEATURE
<222> LOCATION: (23)..(23)
<223> OTHER INFORMATION: proline at position 23 is a hydroxyproline
<220> FEATURE:
<221> NAME/KEY: MISC_FEATURE
<222> LOCATION: (26)..(26)
<223> OTHER INFORMATION: proline at position 26 is a hydroxyproline
<220> FEATURE:
<221> NAME/KEY: MISC_FEATURE
<222> LOCATION: (29)..(29)
<223> OTHER INFORMATION: proline at position 29 is a hydroxyproline

<400> SEQUENCE: 4

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly Ser Gly
            20                  25                  30

Ser Gly Ser Gly Tyr Ile Gly Ser Arg
        35                  40

<210> SEQ ID NO 5
<211> LENGTH: 40
<212> TYPE: PRT
<213> ORGANISM: artificial
<220> FEATURE:
<223> OTHER INFORMATION: collagen mimetic peptide conjugate
<220> FEATURE:
<221> NAME/KEY: MISC_FEATURE
<222> LOCATION: (2)..(2)
<223> OTHER INFORMATION: proline at position 2 is a hydroxyproline
<220> FEATURE:
<221> NAME/KEY: MISC_FEATURE
<222> LOCATION: (5)..(5)
<223> OTHER INFORMATION: proline at position 5 is a hydroxyproline
<220> FEATURE:
<221> NAME/KEY: MISC_FEATURE
<222> LOCATION: (8)..(8)
<223> OTHER INFORMATION: proline at position 8 is a hydroxyproline
<220> FEATURE:
<221> NAME/KEY: MISC_FEATURE
<222> LOCATION: (11)..(11)
<223> OTHER INFORMATION: proline at position 11 is a hydroxyproline
<220> FEATURE:
<221> NAME/KEY: MISC_FEATURE
<222> LOCATION: (14)..(14)
<223> OTHER INFORMATION: proline at position 14 is a hydroxyproline
<220> FEATURE:
<221> NAME/KEY: MISC_FEATURE
<222> LOCATION: (17)..(17)
<223> OTHER INFORMATION: proline at position 17 is a hydroxyproline
<220> FEATURE:
<221> NAME/KEY: MISC_FEATURE
<222> LOCATION: (20)..(20)
<223> OTHER INFORMATION: proline at position 20 is a hydroxyproline
<220> FEATURE:
<221> NAME/KEY: MISC_FEATURE
<222> LOCATION: (23)..(23)
<223> OTHER INFORMATION: proline at position 23 is a hydroxyproline
<220> FEATURE:
<221> NAME/KEY: MISC_FEATURE
<222> LOCATION: (26)..(26)
<223> OTHER INFORMATION: proline at position 26 is a hydroxyproline
<220> FEATURE:
<221> NAME/KEY: MISC_FEATURE
<222> LOCATION: (29)..(29)
<223> OTHER INFORMATION: proline at position 29 is a hydroxyproline

<400> SEQUENCE: 5

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly Ile Lys
```

```
                    20                  25                  30

Val Ala Val Tyr Ile Gly Ser Arg
            35                  40

<210> SEQ ID NO 6
<211> LENGTH: 6
<212> TYPE: PRT
<213> ORGANISM: artificial
<220> FEATURE:
<223> OTHER INFORMATION: flexible peptide linker

<400> SEQUENCE: 6

Ser Gly Ser Gly Ser Gly
1               5
```